United States Patent
Saettone et al.

[11] Patent Number: 6,056,950
[45] Date of Patent: May 2, 2000

[54] OPHTHALMIC SOLUTIONS VISCOSIFIED WITH TAMARIND SEED POLYSACCHARIDE

[75] Inventors: Marco Fabrizio Saettone; Susi Burgalassi; Boris Giannaccini; Enrico Boldrini; Pietro Bianchini; Giulio Luciani, all of Pisa, Italy

[73] Assignee: Farmigea S.p.A., Pisa, Italy

[21] Appl. No.: 09/117,728

[22] PCT Filed: Feb. 4, 1997

[86] PCT No.: PCT/IT97/00026
§ 371 Date: Aug. 5, 1998
§ 102(e) Date: Aug. 5, 1998

[87] PCT Pub. No.: WO97/28787
PCT Pub. Date: Aug. 14, 1997

[30] Foreign Application Priority Data

Feb. 5, 1996 [IT] Italy .................. RM96A0075

[51] Int. Cl.[7] .................................................. A61K 31/74
[52] U.S. Cl. .................................................. 424/78.04
[58] Field of Search ..................................... 424/78.04

[56] References Cited

FOREIGN PATENT DOCUMENTS

WO85/03640 8/1985 WIPO.

OTHER PUBLICATIONS

*Database WPI*, Week 9517, Derwent Publications Ltd., London, GB; AN 95–126104 XP002030113 & JP 07 048 278 A (Taiho Pharm Co., Ltd.), Feb. 12, 1995.

*Primary Examiner*—Carlos Azpura
*Attorney, Agent, or Firm*—Smith, Gambrell & Russell

[57] ABSTRACT

The polysaccharide fraction of tamarind gum, a product of natural origin obtained from the seeds of Tamarindus indica, is used for the production of a thickened ophthalmic solution having a pseudoplastic rheological behaviour and mucoadhesive properties. Said solution is useful as artificial tear and as vehicle for sustained release ophthalmic drugs. The concentrations of tamarind seed polysaccharide preferably employed in ophthalmic preparations for use as artificial tears, i.e. as products for replacing and stabilising the natural tear fluid, particularly indicated for the treatment of dry eye syndrome, are comprised between 0.7 and 1.5% by weight. The concentrations of tamarind seed polysaccharide preferably employed in the production of vehicles (i.e. delivery systems) for ophthalmic drugs, having the function of prolonging the permanence time of said medicaments at their site of action, are comprised between 1 and 4% by weight.

27 Claims, 7 Drawing Sheets

OPHTHALMIC SOLUTIONS VISCOSIFIED WITH TAMARIND SEED POLYSACCHARIDE

This application is filed under 35 USC 371 of PCT/IT97/00026 filed Feb. 4, 1997.

SPECIFICATION

The present invention concerns ophthalmic solutions viscosified with tamarind seed polysaccharide. More specifically, the invention relates to the use of a natural polysaccharide, which is contained in high amounts in the material of natural origin known as tamarind gum, as viscosity enhancer for preparations to be administered into the conjunctival sac. Said polysaccharide may be used for replacing and stabilising the natural tear fluid, or as a vehicle for ophthalmic medicaments, with the function of prolonging the residence time of said medicaments at the site of action, so as to enhance their activity.

BACKGROUND OF THE INVENTION

As it is known, ocular tear fluid is an organised liquid structure which coats the conjunctiva and the exposed surface of the eyeball. In normal conditions, the tear film appears to be a complex three-layered structure, comprising:

- an internal layer of mucus, consisting of a mixture of glycoproteins (mucin) produced by specialised cells (i.e. the conjunctival goblet cells) which are present in the conjunctival epithelium—said layer is adsorbed on the cornea, thus forming a hydrophilic surface;
- a thick intermediate aqueous layer, spread over said hydrophilic surface, consisting essentially of water, electrolytes, proteins, enzymes and mucin;
- a thin external lipid layer, having the main function of controlling the water evaporation rate from the tear film.

The eyelids movement squeezes the mucus out of the conjunctival cells and introduces it into the fornices, and from there the mucus is uniformly distributed on the whole corneal surface by the blinking movements of the eyes.

The three-layers structure described above constitutes a complex physiological system, mainly directed to protect the eye surface, to maintain the hydration, the lubrication and the clearness of the corneal surface, and to cooperate in producing a correct vision. The perfect equilibrium and continuous renovation of said physiological system is a necessary condition for it to be able to carry out said functions. For the said equilibrium and renovation to be realised, a constant but not excessive water evaporation from the tear fluid must take place, so as to keep the osmolarity thereof to the physiological level of about 300 mOsm/l, and the tear film must be continuously redistributed on the corneal surface as a result of blinking.

The integrity of the internal mucin layer represents one of the essential elements of the maintenance of the tear film stability. This because mucin enhances the wettability of the corneal surface, allows the aqueous film to keep adhering to the exposed surface in a continuous and homogeneous way, thus safeguarding its stability, and increases the viscosity of the lacrimal fluid, preventing it from flowing away too rapidly from the conjunctival sac. When mucin is absent or insufficient the cornea becomes non-wettable and, as a consequence of the unbalance between electrolytes and glycoproteins present, the tear film becomes unstable and subject to breaking, with formation of dry areas.

Various diseases or abnormal conditions of the eye manifest themselves with discontinuities of the tear fluid, as a result, e.g., of an insufficient blink frequency, of the prolonged use of contact lenses, of the administration of some systemic drugs or, more frequently, of a senile hyposecretion. In this connection, the term "dry eye" syndrome is commonly used to refer to the ophthalmic condition resulting from the reduction or the instability of the tear film while, more properly, the typical alterations of the corneal surface occurring in this connection are referred to by the term "*keratoconjunctivitis sicca*".

In such situation a degeneration of the conjunctival cells occurs, resulting in increased desquamation, loss of the cell surface microfolds, breaking of the epithelial cells membrane and reduction of the number of mucin-producing goblet cells. This cellular degeneration, being responsible of the reduction of the density of goblet cells and of the lack of mucin, is held to be the origin of most clinical symptoms occurring in dry eye syndrome, such as dryness, irritation, photophobia and foreign body sensation.

Another phenomenon which is unanimously considered to be a sign of an irregularly structured tear fluid is the reduction of the mucus ferning. In normal conditions, mucus is characterised by crystallizing in a fern pattern when made to evaporate at room temperature from an aqueous solution. The ferning phenomenon, which is believed to result from the interaction of the electrolytes with the high molecular weight glycoproteins of mucus, is evidenced after a short time from the collection of tear mucus from the lower fornix of the conjunctiva. It has been ascertained that the various different ferning patterns (i.e., Type I, uniform ferning; Type II, good amount of ferning with ferns of reduced size and empty spaces; Type III; ferning only partially present, Type IV, ferning absent) are connected with the normal or pathological condition of the tear fluid. A dense ferning, for instance, is considered to be the expression of a perfect equilibrium between mucin and electrolytes, while the partial presence or the absence of tear ferning, which is detected in eyes affected by *keratoconjunctivitis sicca*, denotes a quantitative lack of tear mucus or a qualitative alteration of the glycoproteins or of their environment (i.e., pH, hydration, electrolytic equilibrium).

From a diagnostic point of view, dry eye sindrome may be detected and monitored not only by means of the evaluation of the typical symptoms thereof, but also by means of well established procedures, including, as the most common, the evaluation of lacrimal secretion (Schirmer test), the evaluation of the time needed for the tear film to break after a compete blink (break-up time. BUT), and the evaluation of the color of the corneal surface upon staining with rose bengal or fluorescein.

*Keratoconjunctivitis sicca* is normally treated with liquid ophthalmic preparations generally known as "artificial tears", to be instilled in drops in order to replace or supplement the natural tear production. In the simplest case said preparations have only a moistening effect, as they consist of physiological saline solutions, neutral and isotonic with the lacrimal fluid, based on sodium chloride only or on balanced mixtures of various electrolytes. An example of such a preparation, comprising at least four different ionic species (i.e. potassium, sodium, chloride and bicarbonate) in concentrations suitable to reproduce as faithfully as possible the electrolyte composition of the tear fluid, is disclosed in EP-A-0 205 279. Such preparations, as do the simpler physiological solutions, reach the objects of increasing the tear volume, moistening the ocular surface, diluting the mucus deposits and washing away any debris and foreign bodies. However, as the physiological solutions, said preparations have an extremely short duration of action (of the order of a few minutes), since the solution readily drains into the conjunctival sac. As a consequence, the instillation must be repeated every 10–15 minutes, and this brings about the patients' "non-compliance". In addition, a toxic action on the ocular tissues (conjunctiva and cornea) is exerted by the preservatives normally present in the composition.

In order to overcome the drawback mentioned above, artificial tear preparations have been introduced, which are made viscous by the addition of high molecular weight agents, such as, usually, water-soluble polymers of a synthetic, semi-synthetic or natural origin. For instance, U.S. Pat. No. 4,409,205 discloses a composition for ophthalmic use, which can serve both as an artificial tear substance and as a carrier for therapeutically active agents, wherein the viscosity enhancing agent is a non-ionic synthetic polymer, selected between polyvinyl alcohol, polyethylene glycol and mixtures thereof.

However, it has been found that, for said viscosity enhancers to confer advantageous features to a composition for use as artificial tear, is not sufficient that said viscosity enhancers generically increase the viscosity of the product, but it is also necessary that the dispersions thus formed have properties as close as possible to those of mucin dispersions. Namely, said dispersions must behave as much as possible as mucomimetic substances. This requires, fist of all, a particular rheological behaviour, i.e. non-newtonian, similar to the rheological behaviour of natural tears (see, e.g., Bothner et al., Drug Dev. Ind. Pharm., 16, 755–768, 1990). As a matter of fact, it has been shown experimentally that an artificial tear, in order to have a prolonged residence time on the corneal surface while being, at the same time, well tolerated by the patient, must not have a constant viscosity, as newtonian fluids do, but must behave as a non-newtonian pseudoplastic fluid (shear-thinning fluid), i.e. it must show a decrease of viscosity with increasing shear rate. Only such type of rheology may offer a high viscosity in the precorneal tear film at rest, so that in the absence of any stress the film adheres on the corneal surface without dropping, and, at the same time, may provide a low viscosity in the tear film during a blinking movement, when the film is subjected to a shear stress, so that the ophthalmic solution is well tolerated, and is distributed by blinking on the whole corneal surface without being massively displaced, due to friction, towards the lower eyelid rim.

The products having such pseudoplastic behaviour are characterised by a typical flow curve (i.e. the curve obtained by plotting the shear stress versus the shear rate or velocity gradient, and whose slope in each point corresponds to the viscosity value) which deviates from the straight line passing through the origin (corresponding to newtonian flow) in that it is curved with its concavity facing downwards. Such pattern corresponds to a deviation from the newtonian character in the sense of an increasing thinning with increasing shear rate.

Only a few of the macromolecular agents proposed up to now as viscosifiers for artificial tears are actually able to show a non-newtonian behaviour of the pseudoplastic type: for instance, the polyvinyl alcohol proposed by the U.S. patent document cited above gives rise, within ordinary ranges of concentration and molecular weight, to solutions which are practically newtonian.

Examples of compositions for use as artificial tears having non-newtonian rheologic behaviour are disclosed in WO-A-8404681 and in U.S. Pat. No. 5,106,615. The first document proposes the use of carboxyvinyl polymers such as Carbopol®, to be included in the formulation in amounts from 0.05 to 0.25% by weight, as viscosity enhancing agents for ophthalmic solutions. The resulting solutions show, according to the said document, a non-newtonian behaviour which is currently defined as "plastic", characterised by a yield value for the shear stress, below which value no flow occurs. U.S. Pat. No. 5,106,615 discloses compositions useful both as artificial tears and as carriers for ophthalmic medicaments, which are viscosified with anionic polymers of high molecular weight (comprised between 500,000 and 4,000,000). Among the latter, the carboxyvinyl polymers mentioned above and hyaluronic acid are mentioned as preferred. Hyaluronic acid is a polysaccharide of natural origin present in many tissues and fluids, both human and animal, and largely employed in ophthalmic preparations, owing to the marked pseudoplastic behaviour of its aqueous solutions. Equally diffused as thickening agents and viscosity enhancers capable of imparting to the resulting composition the desired non-newtonian rheology are the cellulose esters, such as methylcellulose and the alcoholic derivatives thereof, e.g. hydroxypropylcellulose and hydroxypropylmethylcellulose.

As pointed out in the foregoing, in order to suitably replace and mimic the mucin component of the tear fluid, a product for use as ophthalmic solution must not only show a pseudoplastic rheological behaviour, but also it must show other properties similar to those of mucin. Among such properties there are the ability of wetting the corneal surface, which is intrinsically hydrophobic, thus increasing the uniform spreading of the tear fluid, and the ability of maintaining the integrity of the layer of tear fluid which covers the ocular surface. All that taking into account that the eye receiving the administration of an artificial tear is normally an eye with poor tear secretion, whose tear fluid contains a scarce amount of mucin. Although the products referred to above are endowed with valuable mucomimetic properties, still a good amount of product is to be administered, with a good frequency (from 6 to 12 times a day). As a consequence, the patient is still exposed to the risk of damages deriving from the preservatives which are normally present, often in combination with each other, in multiple-dose bottles.

For the above reasons there have been proposed, for the treatment of *keratoconjunctivits sicca,* erodible ocular inserts to be placed in the conjunctival sac. Said inserts consist, e.g., of small cylinders made of hydroxypropylcellulose which, dissolving in the conjunctival sac, continuously provide the viscosifying and lubricating mucomimetic substance. Although such inserts have the advantage of being totally free of preservatives, they can be difficult to insert, and their presence in the conjunctival sac adds to the foreign body sensation, which is always present in cases of dry eye syndrome. Furthermore, the erodible conjunctival inserts cause temporary vision disturbance, owing to the excess of polymer on the corneal surface.

In order to obtain an enhanced and prolonged lubricating action, the use of products in gel form has also been proposed (e.g., hyaluronic acid or carboxymethylcellulose gel products). However, said preparations have the drawback of blurring the vision and, therefore, they cannot be used when awake, but only while sleeping.

BRIEF SUMMARY OF THE INVENTION

Accordingly, it is an object of the present invention to provide an ophthalmic preparation for use as artificial tear solution, having suitable mucomimetic properties and, specifically, a pseudoplastic rheological behaviour, which, while being relatively cheap both in terms of starting material and in terms of manufacturing process, show an optimal performance as tear fluid substitute, and may also be advantageously employed as vehicle in ophthalmic medicaments, in order to prolong the residence time of therapeutic agents in the tear film.

To this aim there is proposed, in accordance with the present invention, to employ as viscosity enhancer a natural polysaccharide polymer obtained from the seeds of the tamarind tree, i.e. *Tamarindus indica*. Aqueous solutions of the said product exhibit typical pseudoplastic flow properties, with high viscosity at rest and progressively decreasing viscosity at increasing values of the shear rate. In addition, such aqueous solutions show an optimal stabilizing action on the lacrimal fluid. Furthermore, the concerned polysaccharide is endowed with marked mucoadhesive properties, which allow the formation of bonds of various nature with the mucin glycoproteins. As a result, the polysaccharide may reside for quite a long time in the tear fluid and can concentrate at the site where mucin is naturally present, thus expressing at best its mucomimetic properties.

DETAILED DESCRIPTION OF THE INVENTION

As it is known, tamarind tree is widespread in India, Africa and in the whole South East Asia, where it is cultivated primarily for food production, specifically for the production of preserves, extracts, sauces (i.e. chutney) and confections, starting from the fruit pulp. The seed, which was considered originally a by-product, has found various applications, once ground to the powder form (known as "tamarind gum" or "tamarind kernel powder"). The most important of such applications are in textile industry and in paper industry, where tamarind gum is employed as sizing agent, and in food industry, where it is used as thickening, getting, stabilising and binding agent in any kind of products, as do other polysaccharide products such as alginates, pectines, guar gum or locust bean gum. Tamarind kernel powder, which is commercially available as such, contains from 65 to 73% by weight of polysaccharide, from 15 to 23% of protein material, from 3 to 8% of fats and oil and from 2 to 4% of ashes, besides minor amounts of crude fibre, tannins and other impurities.

To date, no applications are known of the polysaccharide purified from tamarind gum as viscosity enhancer in pharmaceutical formulations for ophthalmic use, or in artificial tears.

The PCT application WO-A-85 03640 discloses composite delivery systems, primarily intended for parenteral administration, consisting of liposomes containing an entrapped biologically active ingredient, which are in turn incorporated in a gel matrix. According to the disclosure, the gel matrix has the main purpose of inhibiting the dispersion and the clearance of the liposomes without blocking the delivery of the active ingredient therefrom, and may be made of any one of the materials known as gel-forming agents. Most of the known polysaccharide thickening/gelling agents are mentioned as possible ingredients of the gel matrix, including tamarind gum.

The Japanese patent application JP-A-7 048278 discloses a topical composition for nasal administration which is capable of a prolonged permanence on the nasal mucous membrane, and is characterised by the presence of Tamarind gum or Xanthan gum. The document exclusively refers to a product prepared in powder form.

Besides the above proposed pharmaceutical uses of tamarind gum, the fact that the said gum has been used since long time as food additive is a good evidence of its lack of toxicity, also towards the ocular tissues (acute toxicity studies have been published, e.g., by T. Noda et al. in Seikatsu Eisei, 32(3), 110–15, 1988).

The mucomimetic properties that the polysaccharide fraction of tamarind gum appears to possess, as shown by the experimentation carried out in the frame of the present invention, also include the "ferning" feature mentioned above. Accordingly, said polysaccharide fraction is able to turn, by evaporation, into crystalline products having a morphology quite similar to that of crystallized tear mucus. To this issue, it is to be noted that the only product presently in use as artificial tear known to have good ferning properties is hyaluronic acid.

Another non secondary aspect contributing to render tamarind seed polysaccharide an optimal starting material for the production of artificial tears and of topical ophthalmic products in general is the fact that solutions of said polysaccharide can be subjected to sterilisation by autoclaving (for instance, at 120° C. for 20 minutes) without undergoing any thermal degradation. No similar resistance is shown, e.g., by hyaluronic acid solutions. Owing to the risk of thermal degradation, ophthalmic solutions are normally sterilised by sterile filtration processes, which are difficult to carry out on viscous products such as artificial tears or vehicles for sustained release ophthalmic drugs. The possibility of sterilisation by simple autoclaving makes the preparations based on tamarind seed polysaccharide particularly advantageous from the point of view of manufacture.

Therefore, the present invention specifically provides the use of the polysaccharide fraction of tamarind gum for the production of a viscosified ophthalmic solution for use as an artificial tear or as a vehicle for sustained release of topical ophthalmic medicaments. The invention further provides ophthalmic preparations, i.e. artificial tear solutions and ophthalmic vehicles, containing, as a viscosity enhancing and mucoadhesive agent, a purified polysaccharide fraction of tamarind gum. The term "polysaccharide fraction of tamarind gum", as used in this application, means any polysaccharide-enriched fraction obtainable from tamarind gum (i.e. tamarind kernel powder), the latter being the raw product currently available on the market. A partially purified polysaccharide fraction of tamarind gum is sold, for instance, by Dainippon Pharmaceutical Co. LTD of Osaka, Japan, under the trade name Glyloid®. For the purpose of the present invention, however, the concerned polysaccharide fraction is preferably further purified to give a practically pure tamarind seed polysaccharide.

The amounts of polysaccharide fraction of tamarind gum which are included in the high or low viscosity ophthalmic solutions according to this invention are preferably in the range from 0.1 to 5.0% by weight, more preferably from 0.5 to 3.0 by weight.

Specifically, as concerns the preparations for use as artificial tears, the concentrations of polysaccharide fraction of tamarind gum that offer the best performance are from 0,7 to 1,5% by weight, the optimal concentration being 1% by weight. An artificial tear solution with such a concentration of tamarind seed polysaccharide shows a sufficient viscosity for it to be retained in the eye without being rapidly drained by the nasolacrimal duct, as it happens, as pointed out before, to non-viscosified physiological solutions. On the other hand, said viscosity is not so high as to interfere with vision, and the formulation does not involve the inconvenience typical of gel products. The viscosity of 1 wt. % solutions, moreover, allows an easy dosage of the artificial tear solution in unit-dose containers, which, as it is known, avoid the need to add preservatives to the product. In addition, the viscosity of 1 wt. % solutions results in a smooth filterability (0.8 μm filter), for the clarification of the solution before packaging.

The 1 wt. % solutions of polysaccharide fraction of tamarind gum also show a viscosity quite stable in the pH range of 5.5–8, i.e. around neutrality. Said viscosity rapidly decreases passing to more acidic pH values. This behaviour appears to be extremely advantageous for the use as a topical ophthalmic product, as the preparation may be formulated and administered at acidic pH (e.g., pH=4.5), and thus at reduced viscosity (e.g., 225 mPa.s). Viscosity will increase (e.g., to 297 mPa.s) once the product is in the eye, owing to the higher pH value of the tear fluid (pH=7.4). The foregoing feature is particularly important as it allows, added to the mucoadhesive properties of the tamarind seed polysaccharide, to markedly prolong the residence time of the solution in the precorneal area.

As set forth before, the polysaccharide fraction of tamarind gum according to the invention may also be used as a vehicle for sustained-release ophthalmic medicaments, having the function of increasing the residence time of the said medicaments in the tear film (precorneal area). The viscous and mucoadhesive polysaccharide is actually able to keep the active ingredient of the medicament in contact with the site of action for a prolonged period, thus enhancing the effectiveness of said active ingredient. In the use as a vehicle (i.e., as delivery system) for sustained release topical ophthalmic medicaments, the polysaccharide fraction of tamarind gum may advantageously be employed at a concentration ranging from 1 to 4% by weight. Said concentration is preferably from 1.5 to 2.5% by weight when the vehicle is in liquid form, and from 3 to 4% by weight when it is desired to obtain a vehicle in gel form.

The vehicle may be used as "delivery system" for a large number of ophthalmic drugs to be administered by instillation in the conjunctival sac, which should have a long residence time in the precorneal area to perform their action at best. Possible active ingredients that may exploit the tamarind seed polysaccharide as sustained release vehicle are antiglaucoma and miotic agents, such as pilocarpine and timolol, steroidal antiinflammatory agents, such as dexamethason, non steroidal antiinflammatory agents, such as diclofenac, antimicrobials such as gentamicin, ofloxacin or cloramphenicol, decongesting and antiallergic products such as nafazolin, as well as the various combinations thereof.

Thus, according to a preferred embodiment, the present invention provides the use of the polysaccharide fraction of tamarind gum for the production of a sustained release topical ophthalmic medicament, containing an effective amount of one or more pharmaceutically active ingredients and said polysaccharide fraction as a delivery system. The invention further provides the sustained release ophthalmic medicament thus formulated starting from a purified polysaccharide fraction of tamarind gum. As a general rule, said medicament preferably contains from 1 to 4% by weight of polysaccharide fraction of tamarind gum, together with an effective amount of the pharmaceutically active substance(s) and with other optional formulatory ingredients (i.e. excipients) known in the art, such as those specified below.

Both in the artificial tear formulations and in the formulations for use as delivery system for topical ophthalmic drugs, one or more tonicity adjusting agents should be added, so as to give the solution a correct value of osmolarity. Actually, the solution containing the polysaccharide only, at the preferred concentrations mentioned above, is hypotonic with respect to the lacrimal fluid. Any one of the products currently employed in the art as tonicity agents may be used, such as, for instance, sodium chloride, potassium chloride, mannitol, dextrose, boric acid, propylene glycol.

Other ingredients which may be included in the formulation, in accordance with the known art, are acids or bases as pH adjusting agents, as well as buffers, such as, e.g. the monosodium phosphate—disodium phosphate system or the acetate—acetic acid system. The composition may also comprise preservatives and antimicrobial agents, such as benzalkonium chloride, sodium merthiolate or thimerosal, methyl-, ethyl- and propyl paraben, chlorobutanol, as well as chelating agents such as the edetates or EDTA. Owing to the problems of tolerability mentioned in the foregoing, it is preferred not to include preservatives in the formulations for use as artificial tears. This is clearly possible when the product is packaged in unit-dose containers. In some cases, however, and specially when the product is in multiple dose containers, the addition of preservatives is necessary.

The tamarind seed polysaccharide may be obtained, as set forth before, by purifying commercial tamarind gum (or tamarind kernel powder, also referred to in some instances as "TSKP", tamarind seed kernel powder). the latter is produced by pulverizing the seeds of *Tamarindus indica,* according to technologies first developed in India. According to the Indian patent No. 29620, of 1943, the seeds are heated to 150° C. for 10–15 minutes to parch their external husk, or "testa". Decortication of the seeds is the main problem of the manufacturing process, as the testae are tenaciously attached to the endosperm. According to the method disclosed in the said patent, as a result of parching the testa becomes brittle and can be eliminated by crushing the seeds and blowing off the more finely divided husk fraction. The seed endosperm so obtained is washed, dried and milled, to give raw tamarind gum. According to the Indian patents Nos. 30321 e 30487, respectively of 1943 and 1944, the initial drying operation is not necessary, and the seed can be ground without any previous heating, since the difference in pulverizability between testa and endosperm is so marked that direct grinding results in a material with two different particle sizes. The finer powder resulting from the pulverized testa can be easily separated from said material by screening or by air-classification. The coarse endosperm fragments resulting from the separation are then subjected to further milling.

The powder so obtained has the average composition referred to in the foregoing, and appears as a non free-flowing material, creamy white to light tan, with a characteristic fatty odor, dispersible but not entirely soluble in cold water. For the use as proposed in the instant application said product must be purified, as thoroughly as possible, from the fat and protein components, as well as from the fiber, so as to obtain a polysaccharide-enriched fraction. The practically pure polysaccharide is a free-flowing pale, creamy white powder, without taste or odor.

A method for the production of purified tamarind seed polysaccharide suitable for use in the ophthalmic preparations according to the invention, starting form commercially available partially purified tamarind gum products (such as, e.g., Glyloid® 3S, Dainippon Pharmaceutical Co.) consists in dispersing the starting material in cold deionised water, while stirring for 12 hours so as to obtain a homogeneous dispersion. In order to separate by precipitation any possible proteins present, the dispersion so obtained is heated for 30 minutes at 80° C. and, after cooling, is subjected to centrifugation for 30 minutes at 5000 r.p.m. The supernatant solution is then dialysed against water for at least 48 hours at 4° C., using 12,000–14,000 daltons cut-off membranes. The resulting solution is finally lyophilised, giving a translucid, white final product, totally soluble in water. The absence of contaminating proteins is verified by polyacrylamide gel electrophoresis with sodium dodecyl sulphate (SDS-PAGE).

Other purification processes are also known in the art, specifically in connection with the use of tamarind gum or tamarind seed polysaccharide in other industrial fields. For the pharmaceutical application according to this invention the polysaccharide may also be advantageously purified with any advanced separation and purification processes suitable for eliminating traces of proteins or of other contaminating substances, which may offer products of a particularly high purity.

According to several studies carried out on the structure of the polysaccharide fraction of tamarind gum, it is ascertained that tamarind seed polysaccharide consists of a main chain of glucopyranosyl units bound to each other through (1→4) linkages, with short side chains consisting of xylopyranosyl units attached to the main chain through (1→6) linkages. Said xylopyranosyl units are single, or they may be bound, in turn, to single galactopyranosyl units through a (1→2) linkage. The exact distribution of the xylose or xylose-galactose branches has not yet been ascertained. The ratios glucose:xylose:galactose have been reported to be 3:2:1 by some authors, 4:3:1-1,5 by others and 2,8:2,25:1 by others. The further presence of arabinofuranosyl units has also been reported by some researches. The average molecular weight of the purified polysaccharide has been reported to be around 52,000–56,000 or around 115,000, depending on the method adopted for the measurement. Detailed information about the characterisation of tamarind seed polysaccharide as carried out in the frame of the present invention is given further below.

The present invention is also disclosed by the following non-limiting examples, concerning some specific embodiments thereof. Said embodiments illustrate formulations for use, respectively, as artificial tears (series 1) and as vehicle in topical ophthalmic medicaments (series 2). The polysaccharide-enriched fraction of tamarind gum employed in the following examples is actually the purified tamarind seed polysaccharide produced by the purification process as previously described. Said product will be referred to as TSP, tamarind seed polysaccharide.

EXAMPLES 1.1–1.4—Artificial tear formulations

Example 1.1

| Ingredients | % by weight |
| --- | --- |
| TSP | 1.00 |
| mannitol | 5.04 |
| deionised water | q.s. to 100 |
| HCl, 1N | q.s. to pH 4.5 ± 0.2 |

The product is prepared by the following steps:
the necessary amount of TSP is weighed in a suitable glass vessel;
90% of the available water is added, and the mixture is stirred for some hours, until complete dissolution of the product;
the fixed amount of mannitol is added, while keeping stirring, and the mixture is left under stirring until complete dissolution of the product;
deionised water is added up to the final weight (100%);
1 N hydrochloric acid is added to reach the desired pH;
the solution so obtained is sterilised in autoclave.

Example 1.2

| Ingredients | % by weight |
| --- | --- |
| TSP | 1.00 |
| sodium chloride | 0.90 |
| deionised water | q.s. to 100 |

The product is prepared as in example 1.1, by first dissolving TSP, then sodium chloride and finally bringing to the total weight with the remaining deionised water.

Example 1.3

| Ingredients | % by weight |
| --- | --- |
| TSP | 0.70 |
| sodium chloride | 0.85 |
| benzalkonium chloride | 0.01 |
| deionised water | q.s. to 100 |

The product is prepared as in example 1.1, by first dissolving TSP, then sodium chloride and benzalkonium chloride, and finally bringing to the total weight with the remaining deionised water.

Example 1.4

| Ingredients | % by weight |
| --- | --- |
| TSP | 1.50 |
| monosodium phosphate | 0.71 |
| disodium phosphate | 0.09 |
| sodium chloride | 0.50 |
| benzalkonium chloride | 0.01 |
| deionised water | q.s. to 100 |

The product is prepared as in example 1.1, by first dissolving TSP, then monosodium phosphate, disodium phosphate, sodium chloride and benzalkonium chloride, and finally bringing to the total weight with the remaining deionised water.

EXAMPLES 2.1–2.5—Ophthalmic Medicament Formulations

Example 2.1

| Excipient ingredients | % by weight |
| --- | --- |
| TSP | 3.00 |
| mannitol | q.s. to 300 mOsm/l |
| deionised water | q.s. to 100 |

The product is prepared by the following steps:
the necessary amount of TSP is weighed in a suitable glass vessel;

90% of the available water is added, and the mixture is stirred for some hours, until complete dissolution of the product;

the fixed amount of mannitol is added, while keeping stirring, and the mixture is left under stirring until complete dissolution of the product;

the required amount of the desired active ingredient is added while keeping stirring;

deionised water is added up to the final weight (100%);

the solution so obtained is sterilised in autoclave.

Example 2.2

| Excipient ingredients | % by weight |
| --- | --- |
| TSP | 4.00 |
| benzalkonium chloride | 0.01 |
| sodium chloride | q.s. to 300 mOsm/l |
| deionised water | q.s. to 100 |

The product is prepared as in example 2.1, adding sodium chloride and benzalkonium chloride in place of mannitol.

Example 2.3

| Excipient ingredients | % by weight |
| --- | --- |
| TSP | 3.50 |
| monosodium phosphate | 0.71 |
| disodium phosphate | 0.09 |
| disodium edetate | 0.01 |
| benzalkonium chloride | 0.01 |
| sodium chloride | q.s. to 300 mOsm/l |
| dionised water | q.s. to 100 |

The product is prepared as in example 2.1, adding monosodium phosphate, disodium phosphate, disodium edetate, sodium chloride and benzalkonium chloride in place of mannitol.

Example 2.4

| Excipient ingredients | % by weight |
| --- | --- |
| TSP | 2.00 |
| monosodium phosphate | 0.71 |
| disodium phosphate | 0.09 |
| sodium merthiolate | 0.002 |
| disodium edetate | 0.01 |
| sodium chloride | q.s. to 300 mOsm/l |
| deionised water | q.s. to 100 |

The product is prepared as in example 2.3, adding sodium merthiolate in place of benzalkonium chloride.

Example 2.5

| Excipient ingredients | % by weight |
| --- | --- |
| TSP | 1.00 |
| methyl paraben sodium salt | 0.06 |
| mannitol | q.s. to 300 mOsm/l |

Example 2.5 -continued

| Excipient ingredients | % by weight |
| --- | --- |
| NaOH | q.s. to pH 7,4 ± 0.2 |
| deionised water | q.s. to 100 |

The product is prepared by the following steps:

the necessary amount of TSP is weighed in a suitable glass vessel;

90% of the available water is added, and the mixture is stirred for some hours, until complete dissolution of the product;

the fixed amounts of mannitol and methyl paraben sodium salt are added, while keeping stirring, and the mixture is left under stirring until complete dissolution of the product;

the required amount of the desired active ingredient is added while keeping stirring;

deionised water is added up to the final weight (100%);

1 N sodium hydroxide is added to reach the desired pH;

the solution so obtained is sterilised in autoclave.

Some experimental results showing the features of the polysaccharide products according to the invention and the performance of the preparations containing the same are given below.

Characterisation of Tamarind Seed Polysaccharide

Figure 1:
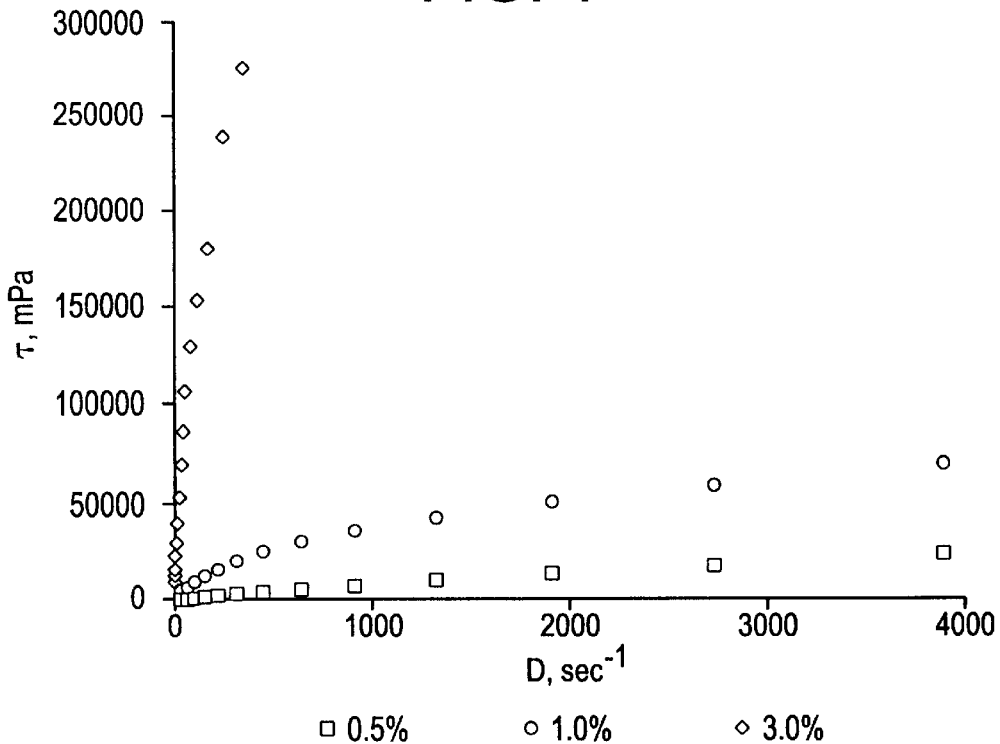
FIG. 1 shows some flow curves (shear stress, $\tau$, in mPa, as a function of shear rate or velocity gradient, D, in $sec^{-1}$) of tamarind seed polysaccharide solutions according to the invention, at various concentrations.

Samples of tamarind seed polysaccharide produced by purifying Glyloid® 3S (Dainippon Pharmaceutical Co.) according to the method described above were analysed to ascertain the structure and properties of the polysaccharide. The polysaccharide composition was determined by gas chromatography in accordance with the method proposed by Blakeney et al. (Carbohydr. Res., 113, 291–299, 1983). The sample was hydrolysed with trifluoroacetic acid at 100° C. for 16 hours and the monosaccharides so obtained were converted to alditol peracetates. The mixture was then analysed with a suitably equipped gas chromatograph, thereby evidencing the presence of four different monosaccharide units, i.e. glucose, xylose, galactose and arabinose. The relative amounts of said monosaccharides were determined by the method of the internal standard, using for that purpose a known amount of inositol in the mixture fed to the chromatograph.

The ratios found were as follows:

Ara:Gal:Xyl:Glc=1.0:4.4:9.0:12.9 with an average standard error of ±3%. The foregoing composition corresponds to the structure hypothesised in the literature (recently confirmed by York et al., Carbohydr. Res., 1993), and can be represented schematically as follows:

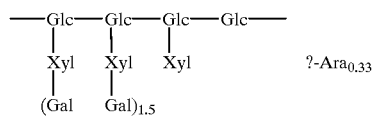

The 1.5 value shown for galactose amounts to the presence of one galactose residue for each unit of four glucose residues plus another galactose residue every other unit of four glucose residues. One arabinose residue appears to be present every three units of four glucose residues.

The polysaccharide was also analysed by FT-IR spectrophotometry (i.e., Fourier transform infrared spectrophotometry). The IR spectrum so obtained shows the presence of the stretching signal of the OH groups (~3000 cm$^{-1}$), of the stretching signals of the ether group of the saccharide ring (i.e., the C—O—C group) and other connected absorbance signals (1205–1041 cm$^{-1}$), as well as the signal attributed to the type β anomeric carbon (such as those present in the main chain), at 896 cm$^{-1}$. The $^1$H NMR and $^{13}$C NMR spectra of the polysaccharide were found to be similar to those reported in the literature for tamarind seed polysaccharide. In particular, from the $^1$H NMR spectrum it appears that the polysaccharide does not have lateral non-saccharide substituent groups, such as acetyl, piruvate or succinate.

Aqueous solutions of tamarind seed polysaccharide at various concentrations were also analysed by exclusion chromatography, and the results obtained have shown the presence of multiple molecular weights with non-regular distributions, whose form is strongly influenced by the polysaccharide concentration and by the presence of salt (NACl) added to the solution. This may be attributed to the existence of an aggregation between the polysaccharide molecules in aqueous solution. In conditions of maximum disaggregation the polysaccharide shows an almost gaussian distribution of molecular weights, with an average value of about 76,500. In conditions of maximum aggregation the average molecular weight found reaches the apparent value of 330,000.

Study of the Rheological Properties

Solutions of the tamarind seed polysaccharide described in the previous section, at various concentrations (0.5, 1.0 and 3.0% by weight), were tested for viscosity using a Rheomat 115 rotational viscosimeter (Contraves) with a MS-O measuring element with coaxial cylinders. Measurements have been carried out at 25° C. The shear stress values τ measured at increasing values of the shear rate D, for two solutions containing 0.5% and 1% by weight of TSP, are indicated in the following table.

TABLE 1

Flow curves of tamarind seed polysaccharide solutions

| | shear stress $\tau_1$ (mPa) | |
|---|---|---|
| shear rate D, (sec$^{-1}$) | TSP 0.5% (w/w) | TSP 1.0% (w/w) |
| 25.60 | 357.12 | 3273.60 |
| 36.64 | 535.68 | 4523.52 |
| 52.39 | 714.24 | 5832.96 |
| 75.01 | 1011.84 | 7797.12 |
| 107.38 | 1368.96 | 10177.92 |
| 153.62 | 1964.16 | 13094.40 |
| 220.23 | 2678.40 | 16725.12 |
| 315.19 | 3630.72 | 20891.52 |
| 450.91 | 4642.56 | 25712.64 |
| 645.29 | 6011.52 | 30652.80 |
| 923.69 | 8035.20 | 36307.20 |
| 1322.40 | 10713.60 | 42556.80 |
| 1894.11 | 14165.76 | 50592.00 |
| 2709.43 | 18629.76 | 59996.16 |
| 3877.71 | 24224.64 | 70590.72 |

Similarly, the shear stress values measured at increasing shear rate for a solution containing 3% by weight of TSP are indicated in the following table.

TABLE 2

Flow curves of 3.0 wt. % TSP solutions

| shear rate D, (sec$^{-1}$) | shear stress τ, (mPa) |
|---|---|
| 2.00 | 9960 |
| 2.86 | 13280 |
| 4.10 | 16600 |
| 5.86 | 23240 |
| 8.39 | 29880 |
| 12.01 | 39840 |
| 17.21 | 53120 |
| 26.64 | 69720 |
| 35.24 | 86320 |
| 50.44 | 106240 |
| 72.20 | 129480 |
| 103.36 | 152720 |
| 148.05 | 179280 |
| 211.77 | 239040 |
| 303.09 | 275560 |

The above numerical data are illustrated in FIG. 1, from which it clearly appears that, at the three concentrations tested, the product shows a non-newtonian rheological behaviour of the pseudoplastic type, characterised by a flow curve with concavity facing downwards. In practice, viscosity markedly decreases when the shear stress increases, so that the product appears to be quite viscous at rest, while for high values of the shear stress (as it happens in the tear fluid during blinking, when values as high as 10,000 s$^{-1}$ are reached) viscosity appears to be quite lower. The solutions tested do not show any thixotropic behaviour, i.e., they do not undergo any reductions of viscosity if the fluid is subjected to the same shear rate for a long period of time.

Figure 2:
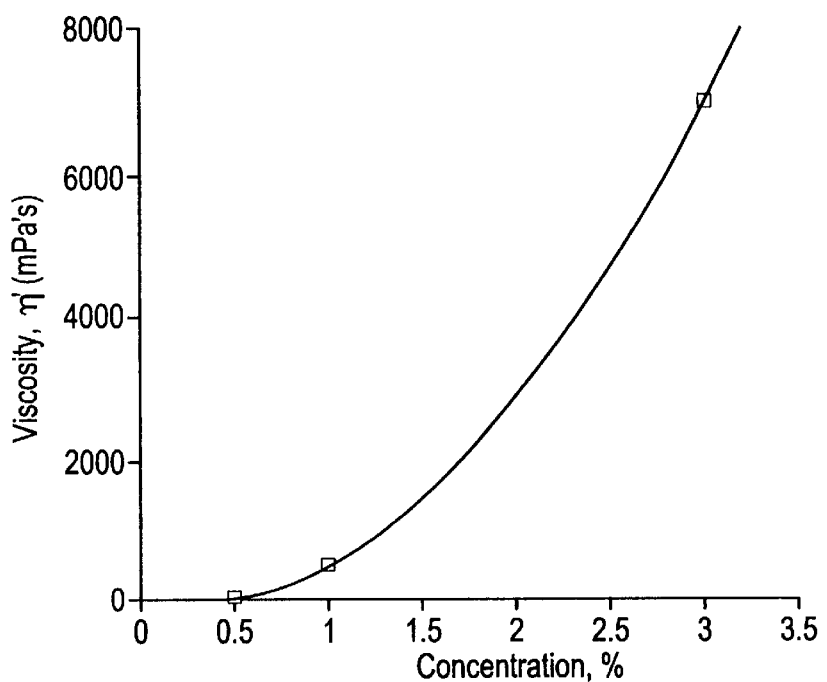
FIG. 2 shows the apparent viscosity ($\eta'$) of TSP solutions as a function of the concentration (percent by weight) of said solutions.

FIG. 1 also shows that there is a sharp increase of viscosity when passing from a TSP concentration of 1% by weight to a concentration of 3%. This feature is better evidenced in FIG. 2, where the apparent viscosity η', in mPa.s, is plotted versus the TSP concentration of the solutions tested. The value of η' has been calculated from logarithmic plots of D versus τ, by extrapolation at velocity gradient D=1. The curve passing through the experimental points on the diagram is well approximated by the following quadratic polynomial equation:

$$y = 870{,}786x^2 - 271{,}859x - 54{,}297.$$

Figure 3:
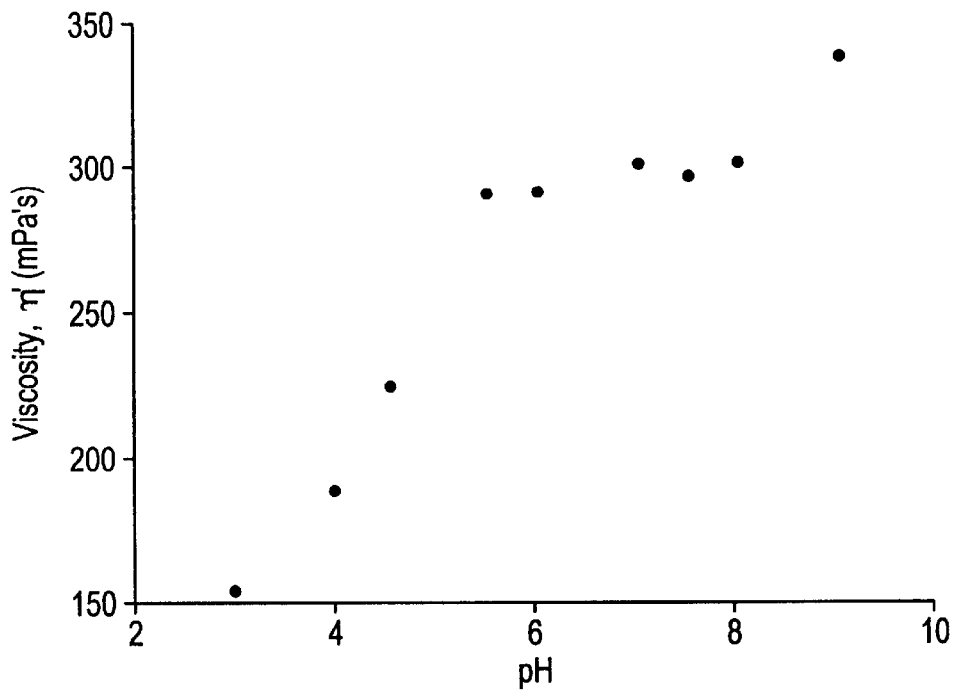
FIG. 3 shows the apparent viscosity ($\eta'$) of a 1 wt. % solution of TSP as a function of pH.

The rheological behaviour of the products according to the invention has also been evaluated at varying pH. It has been found that viscosity is quite stable in an interval around neutrality, and then sharply decreases at increasingly acid pH. Table 3 below and the corresponding FIG. 3 show the apparent viscosity values measured at different pH for a 1 wt. % TSP solution.

TABLE 3

Viscosity of 1.0 wt. % TSP solutions at varying pH

| pH | viscosity η' (mPa · s) |
|---|---|
| 9 | 338.06 |
| 8 | 301.99 |
| 7.5 | 297.17 |
| 7 | 301.30 |
| 6 | 291.74 |
| 5.5 | 291.07 |
| 4.5 | 225.42 |
| 4 | 189.23 |
| 3 | 154.88 |

As noted before, the above effect of pH on viscosity of TSP solutions may be advantageously exploited to carry out industrial handling, packaging and administration of the product at acidic pH, i.e. at low viscosity conditions. Upon instillation in the eye, the product's pH changes to approximately neutral, and the product immediately becomes more viscous.

Figure 4:
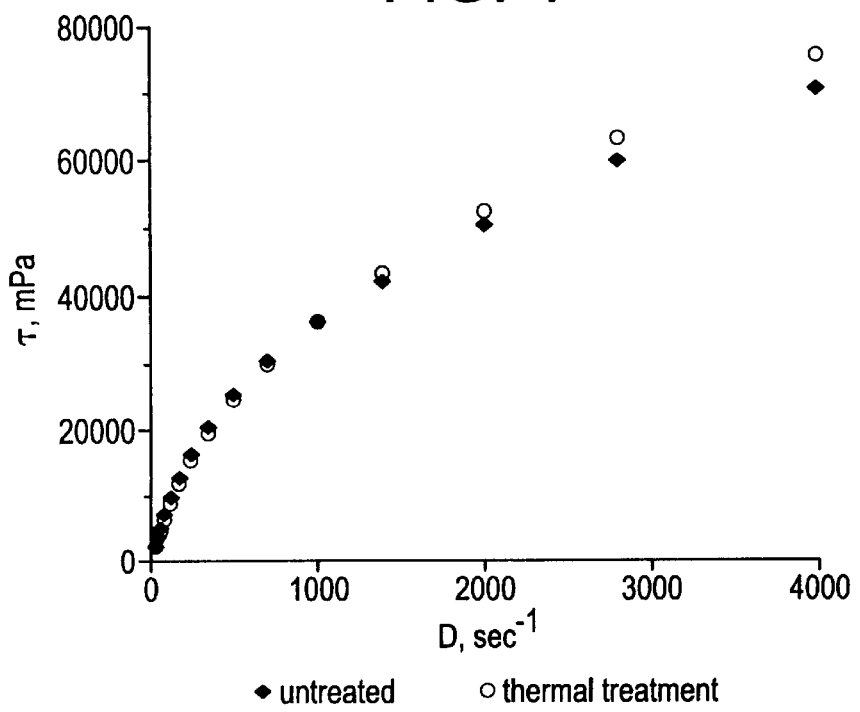
FIG. 4 shows two flow curves of the kind shown in FIG. 1, for a 1 wt. % solution of TSP, before and after sterilisation by autoclaving.

The solutions according to the invention have also been subjected to sterilisation in autoclave, at 120° C. for 20 minutes, and their flow curves have been determined thereafter, in order to evaluate the effect of the thermal treatment on the flow properties of the product. The following table and the corresponding FIG. 4 show, with reference to a 1 wt. % TSP solution, that the pseudoplastic flow behaviour of the polysaccharide products studied is not substantially affected by the thermal treatment. As pointed out before, this property corresponds to a remarkable advantage from the manufacture point of view, since it makes it possible to sterilise the preparation by means of a thermal treatment, instead of the more complex sterile filtration treatment which is normally applied to the prior art products.

TABLE 4

Flow curves of 1.0 wt. % TSP solutions before and after autoclaving

| | shear stress τ, (mPa) | |
|---|---|---|
| shear rate $D_1$ (sec$^{-1}$) | without thermal treatment | with thermal treatment |
| 25.60 | 3273.60 | 2856.96 |
| 36.60 | 4523.52 | 3868.80 |
| 52.40 | 5832.96 | 5237.76 |
| 75.02 | 7797.12 | 7142.40 |
| 107.38 | 10177.92 | 9404.16 |
| 153.62 | 13094.40 | 12320.64 |
| 220.23 | 16725.12 | 15891.84 |
| 315.19 | 20891.52 | 20117.76 |
| 450.91 | 25712.64 | 25117.44 |
| 645.29 | 30652.80 | 30414.72 |
| 923.69 | 36307.20 | 36604.80 |
| 1322.40 | 42556.80 | 43628.16 |
| 1894.11 | 50592.00 | 52556.16 |
| 2709.40 | 59996.16 | 63210.24 |
| 3877.70 | 70590.72 | 75471.36 |

Artificial Tear—Biological Tests

Some of the experiments carried out on animals in order to evaluate the performance in vivo of the products according to the invention as artificial tear preparations are reported below. All of the tests described herein have been carried out on male New Zealand albino rabbits weighing 2–2.5 kg. In these rabbits, *keratoconjunctivitis sicca* has been induced by repeated instillation of 1% (w/w) atropine sulphate (AS). The artificial tear formulation of Example 1.1 (containing 1% by weight of TSP) has been used in the tests as the product of the invention. As specified, this preparation is formulated at pH 4.5–5.0 in order to exploit the viscosity increase after administration.

In a first experiment, performed on 12 rabbits, a drop of AS was instilled in both eyes of the animals 3 times a day for 5 days on end. After 5 minutes from the administration, 50 μl (corresponding to one drop) of the isotonic formulation of Example 1.1, at pH 5.0, were instilled in the right eye only. At the day=2, 3, 4 and 5 from the beginning of the treatment the ocular surface was examined after staining with sodium fluorescein. The examination of the cornea was performed with a slit lamp equipped with blue cobalt filter. The results obtained, on 10 animals or more, are reported in Table 5 below in terms of number of fluorescein-positive eyes (in which intensely colored spots have been observed, corresponding to corneal epithelium alterations) over the total number of eyes examined.

TABLE 5

Tests on animals - Fluorescein staining test

| Time from the beginning of treatment with AS (days) | 2 | 3 | 4 | 5 |
|---|---|---|---|---|
| | no. of eyes positive to fluorescein/total | | | |
| Right eye - (treated) | 0/12 | 0/12 | 0/10 | 0/10 |
| Left eye - (control) | 0/12 | 0/12 | 3/10 | 6/10 |

The above results show that in the eyes treated with the artificial tear solution based on TSP no corneal lesions occurred, contrary to what happened to eyes wherein the atropine-induced dry eye syndrome was not treated.

In another series of tests, the effectiveness of the product containing 1% by weight of tamarind seed polysaccharide (formulation of Example 1.1) as an artificial tear has been evaluated, in comparison with untreated controls and with a commercial product of the prior art, by means of the Schirmer test for lacrimal secretion. Also in this case *keratoconjunctivitis sicca* has been induced by administration of 1% AS 3 times a day for 5 days on end.

The animals were divided into three groups, which were treated as follows.

the animals of the 1st group were given, 5 minutes after the instillation of AS, 50 µl (corresponding to one drop) of the isotonic formulation of Example 1.1, at pH 5.0;

the animals of the 2nd group were given, 5 minutes after the instillation of AS, 50 µl (corresponding to one drop) of a commercial artificial tear thickened with 0.5% by weight hydroxypropylmethylcellulose (HPMC);

the animals of the 3rd group were not treated.

At the day=0, 2, 3, 4 and 5 from the beginning of the treatment the animals underwent the Schirmer test. The scores assigned to the Schirmer test were calculated as follows: 0.278 points for each 5 seconds employed by the tear fluid to reach the height of 10 mm (with a maximum of 10 points in 3 minutes); after 3 minutes, if the filter paper is not soaked up to 10 mm, 10 points are added, +1 point for each mm of paper not soaked. The numerical results of the test are shown in the following table, and the corresponding diagram is illustrated in the enclosed FIG. 5.

TABLE 6

Tests on animals - Schirmer test for lacrimal secretion

| Time | TSP 1% (w/w) | | HPMC 0.5% (w/w) | | Untreated | |
|---|---|---|---|---|---|---|
| (days) | score | std. err. | score | std. err. | score | std. err. |
| 0 | 6.079 | 0.39 | 6.079 | 0.39 | 6.079 | 0.39 |
| 2 | 8.480 | 1.22 | | | 12.000 | 1.26 |
| 3 | 9.230 | 1.24 | 8.430 | 1.12 | 10.320 | 1.28 |
| 4 | 4.540 | 0.64 | 7.640 | 1.23 | 10.790 | 1.71 |
| 5 | 5.190 | 0.92 | 7.950 | 1.09 | 11.290 | 1.57 |

Figure 5:
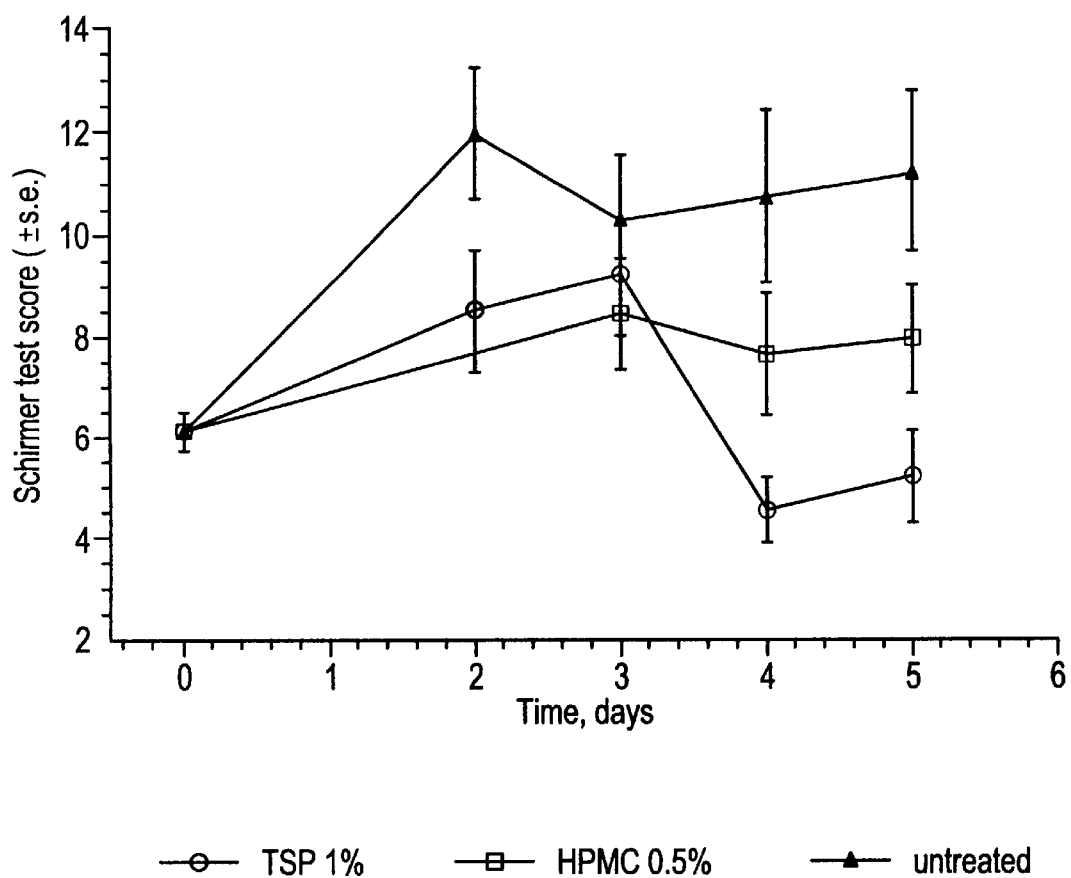
FIG. 5 illustrates the results of the Schirmer test evaluating lacrimal secretion on rabbits with *keratoconjunctivitis sicca*, either treated or not with the product according to the invention.

As it may be noted from the previous data and, more readily, from the graph of FIG. 5, the Schirmer test score for the controls increases in a statistically significant manner since the second day of treatment with atropine sulphate, thus confirming the validity of the method employed for inducing *keratoconjunctivitis sicca*. Also, the results clearly evidence the protecting activity against dry eye possessed by the preparation according to the invention. Said activity appears to be more persistent than that of the prior art artificial tear. Actually, in the test animals receiving the TSP preparation the lacrimal secretion reverts to its baseline value starting from the fourth day of treatment.

Delivery System for Ophthalmic Medicaments—
Biological Tests

The following tests in vivo concern the performance of the tamarind seed polysaccharide according to the invention as a mucoadhesive and viscosity-enhancing vehicle for use in sustained release topical ophthalmic preparations.

Pilocarpine Formulations

A well-known antiglaucoma medicament with miotic activity, i.e. pilocarpine, has been employed in several in vivo tests using rabbits as the animal model. In order to evaluate the performance of the vehicle according to the invention as a delivery system, the precorneal residence time and the miotic activity versus time of pilocarpine preparations containing TSP have been measured. The results obtained are compared with the performance of other formulations, with or without a thickening agent.

Specifically, all of the ophthalmic preparations employed in the tests shown herein contain 2.0% by weight of pilocarpine nitrate ($PiNO_3$), but the control preparation referred to in the following table as RS (i.e. reference solution) is an aqueous solution without any thickening agent, while the preparation according to the invention, referred to below as "TSP", is formulated according to Example 2.1. Each one of the other preparations contain a different polymeric vehicle, as shown in the table.

TABLE 7

Ophthalmic preparations employed in the tests

| Preparation | Active ingredient | Kind and concentration (wt. %) of polymer |
|---|---|---|
| RS | Pi $NO_3$ 2.0% | none |
| TSP | Pi $NO_3$ 2.0% | TSP 3.0% |
| PVA | Pi $NO_3$ 2.0% | polyvinyl alcohol 13% |
| HPMC | Pi $NO_3$ 2.0% | hydroxypropylmethylcellulose 14% |

All of the tests described herein have been carried out on male New Zealand albino rabbits weighing 3–3.5 kg, non anesthesized and kept in standard stabling conditions, at a temperature of 18–20° C. Both the miotic effect and the residence time of the drug in the tear fluid were measured after instillation (at the time=0) of 25 µl of the preparation under study in the lower conjunctival sac of one eye of the rabbits, while the other eye served as a control.

Figure 6:
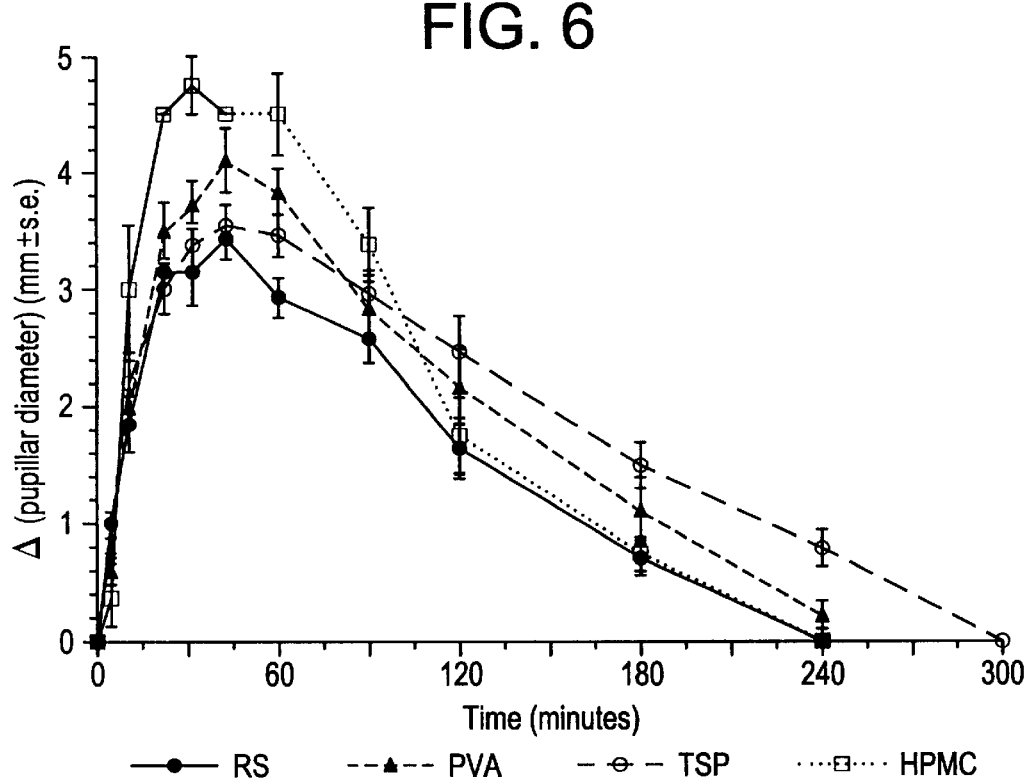
FIG. 6 shows the curves of miotic response [Δ(pupillar diameter)] versus time in rabbits treated with pilocarpine preparations containing or not the product according to the invention.

The variation of pupillar diameter was measured with a micrometer at suitable time intervals, while the intensity of the light source was being manitained constant. FIG. 6 shows a diagram of the miotic response after instillation of each one of the four above ophthalmic preparations. Said response is expressed in terms of variation of the pupillar diameter (in mm) as a function of the time (in min.) elapsed from the instillation of the preparation. The vertical bars on each experimental point represent the standard error. The numerical values corresponding to the curves of FIG. 6 are reported in the following table.

TABLE 8

Miotic response versus time for the tested preparations

| Time | RS | | TSP | | PVA | | HPMC | |
|---|---|---|---|---|---|---|---|---|
| (min.) | Δdiam. (mm) | std. err. | Δdiam. (mm) | std. err. | Δdiam. (mm) | std. err. | Δdiam. (mm) | std. err. |
| 0 | 0.00000 | 0.00000 | 0.00000 | 0.00000 | 0.00000 | 0.00000 | 0.00000 | 0.00000 |
| 5 | 1.00000 | 0.10911 | 0.62500 | 0.13933 | 0.61111 | 0.11111 | 0.37500 | 0.23936 |
| 10 | 1.85710 | 0.23690 | 2.20830 | 0.18928 | 2.00000 | 0.16667 | 3.00000 | 0.54006 |
| 20 | 3.14290 | 0.35714 | 3.00000 | 0.22191 | 3.50000 | 0.23570 | 4.50000 | 0.00000 |

TABLE 8-continued

Miotic response versus time for the tested preparations

| Time | RS | | TSP | | PVA | | HPMC | |
|---|---|---|---|---|---|---|---|---|
| (min.) | Δdiam. (mm) | std. err. | Δdiam. (mm) | std. err. | Δdiam. (mm) | std. err. | Δdiam. (mm) | std. err. |
| 30 | 3.14290 | 0.28272 | 3.37500 | 0.19584 | 3.72220 | 0.20601 | 4.75000 | 0.25000 |
| 40 | 3.42860 | 0.17003 | 3.54170 | 0.17899 | 4.11110 | 0.27358 | 4.50000 | 0.00000 |
| 60 | 2.92860 | 0.17003 | 3.45830 | 0.17899 | 3.83330 | 0.20412 | 4.50000 | 0.35355 |
| 90 | 2.57140 | 0.20203 | 2.95830 | 0.19903 | 2.83330 | 0.28868 | 3.37500 | 0.31458 |
| 120 | 1.64290 | 0.26082 | 2.45830 | 0.30438 | 2.16670 | 0.31180 | 1.75000 | 0.32275 |
| 180 | 0.71429 | 0.14869 | 1.50000 | 0.19462 | 1.11890 | 0.28599 | 0.75000 | 0.14434 |
| 240 | 0.00000 | 0.00000 | 0.79167 | 0.15641 | 0.22222 | 0.12108 | 0.00000 | 0.00000 |
| 300 | | | 0.00000 | 0.00000 | | | | |

As it appears from the curves of FIG. 6, both the prior art preparations, i.e. PVA and HPMC, and the preparation based on tamarind seed polysaccharide according to the invention, i.e. TSP, cause an increase in the miotic response with respect to the reference solution with no thickening agents (RS). The mucoadhesive action of the product contained in the TSP preparation results in an increase of the duration of the miotic response, which lasts up to 300 minutes. Such phenomenon does not occur, or it occurs in a quite negligible measure, with the other vehicles, for which the duration of the miotic response does not extend beyond 240 minutes. It is to be noted, to this regard, that HPMC is commonly considered to be a mucoadhesive substance.

In order to verify whether the product according to the invention was able to prolong, in comparison with other vehicles, the residence of the drug in the precorneal area, the following test was carried out: after instillation of one of the preparations under test, samples of tear fluid (1 μl) were collected, at suitable time intervals, from the rim portion of the lower conjunctival sac, using a microcapillary and avoiding any contact with the corneal epithelium. The tear fluid samples, transferred into microprobes, were diluted with water and analysed by HPLC.

Figure 7:
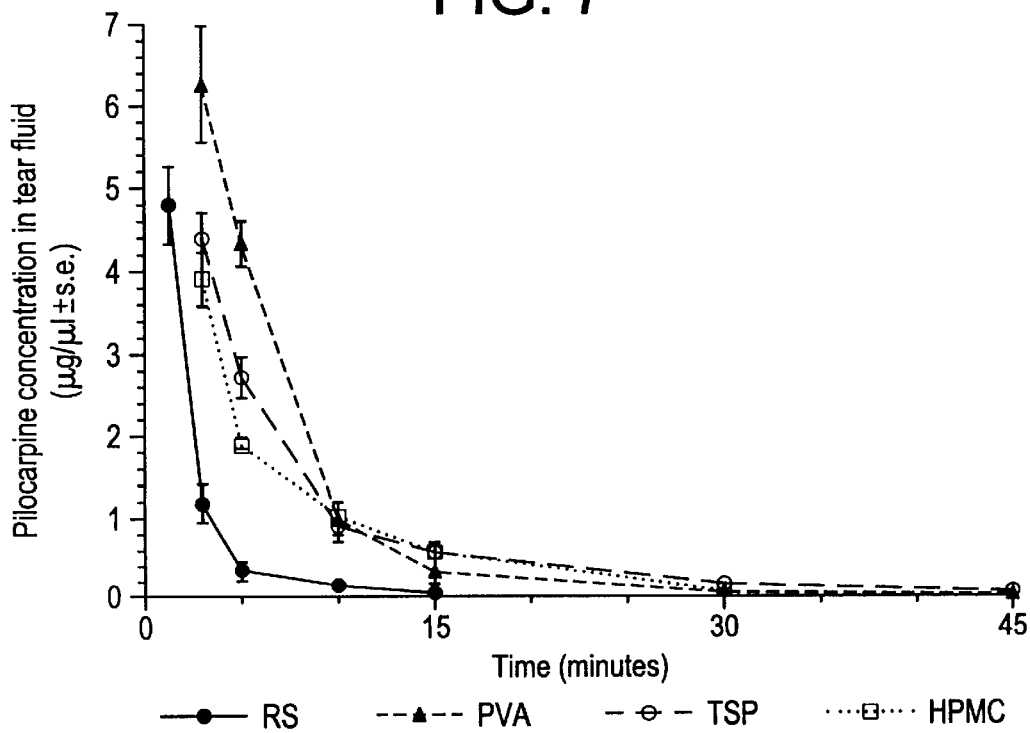
FIG. 7 shows the curves of pilocarpine concentration versus time in the tear fluid of the same rabbits of FIG. 6.

The results of said test are reported, in terms of pilocarpine concentration (μg/μl) detected in the tear fluid as a function of time, in Table 9 and in the corresponding FIG. 7.

macokinetic parameters of pilocarpine in the tear fluid, in the various formulations, as calculated from the tests described above. The said parameters are as follows:

$K_e$: apparent clearance velocity constant

AUC $t_{3min} \to t$: area under the curve of tear fluid drug concentration as a function of time—with integration interval 3 min.→

$AUC_{rel}$: AUC relative to the reference solution $t_{1/2}$: half-life time of the drug in the tear fluid MRT: mean residence time of the drug in the tear fluid.

TABLE 10

Pharmacokinetic parameters of pitocarpine in the tear fluid

| Prepn. | $K_e$ (min$^{-1}$) | AUCt$_{3min} \to t_x$ (min · μg · μl$^{-1}$) | $AUC_{rel}$ | $t_{1/2}$ (min) | MRT (min) |
|---|---|---|---|---|---|
| RS | 0.220 | 3.69 | 1.00 | 3.15 | 6.12 |
| TSP | 0.114 | 27.28 | 7.39 | 6.08 | 9.18 |
| PVA | 0.176 | 34.05 | 9.23 | 3.94 | 5.98 |
| HPMC | 0.098 | 23.13 | 6.27 | 8.83 | 8.83 |

The above data show that the most mucoadhesive vehicles (i.e. TSP and HPMC) cause an increase in the half-life almost of double with respect to the reference solution. A

TABLE 9

Residence time of pilocarpine in the tear fluid

| Time | RS | | TSP | | PVA | | HPMC | |
|---|---|---|---|---|---|---|---|---|
| (min.) | conc. (μg/μl) | std. err. | conc. (μg/μl) | std. err. | conc. (μg/μl) | std. err. | conc. (μg/μl) | std. err. |
| 1 | 4.786000 | 0.467000 | | | | | | |
| 3 | 1.194400 | 0.226610 | 4.377900 | 0.3063000 | 6.245000 | 0.716710 | 3.894000 | 0.320000 |
| 5 | 0.359860 | 0.126810 | 2.720700 | 0.2563300 | 4.322500 | 0.262500 | 1.900000 | 0.038000 |
| 10 | 0.152900 | 0.039897 | 0.924170 | 0.1997100 | 1.018200 | 0.193710 | 1.030000 | 0.086000 |
| 15 | 0.067674 | 0.041353 | 0.590830 | 0.1195000 | 0.330130 | 0.149760 | 0.583000 | 0.077000 |
| 30 | | | 0.175280 | 0.0591650 | 0.059650 | 0.019638 | 0.074000 | 0.005500 |
| 45 | | | 0.060033 | 0.0057391 | 0.028733 | 0.011403 | 0.025000 | 0.001800 |
| 60 | | | | | | | 0.016000 | 0.001790 |

As it may be seen from FIG. 7, after the instillation of the aqueous reference solution of PiNO$_3$ (RS) a rapid reduction of the drug concentration in the lacrimal fluid occurs, while the addition of polymers to the solution gives rise, in all cases, to an increase in the bioavailability of the drug. The differences in the performance of the various vehicles are better evidenced by the following table, reporting the pharmarked increase is also noted in the average residence time of the active ingredient in the tear fluid, said increase being higher for the product according to the invention than for the other vehicles examined. This result, together with what reported above concerning the miotic activity, confirms that the use of tamarind seed polysaccharide as viscosity enhancing and mucoadhesive agent results in prolonging the residence of pilocarpine in the precorneal area, thus prolonging the action of each administered dose of said ophthalmic drug.

Timolol Formulations

Timolol is a β-adrenergic blocker currently used in ophthalmology as a topical antiglaucoma medicament. It is known that the activity of β-blocking agents in the treatment of ocular hypertension is closely related to the presence of the active ingredient in the receptor sites of the ciliary body, where the aqueous humor is produced. On the other hand, after a topical administration of drug on the ocular surface, the drainage of the product through the nasolacrimal duct results in some systemic absorption of the drug. As a consequence, the use of β-blocking agents in topical ophthalmic preparations usually brings about some undesired side effects, such as alterations of the cardiac rhythm, asthma, emphysema and congestive heart failure. The experimental activity reported below was intended to show that the presence of the polysaccharide according to the invention in an ophthalmic preparation based on timolol on one hand increases the ocular bioavailability of the active ingredient and, on the other hand, markedly reduces the absorption of timolol in the blood.

All of the ophthalmic preparations employed in the tests contain about 0.68% by weight of timolol maleate, corresponding to 0.5% by weight of timolol. The preparation referred to in the following table as RS (i.e. reference solution) is a commercial eye-drop preparation without any thickening agent (i.e., Droptimol®), while the preparation referred to as "GELLAN" is a commercial preparation (i.e., Timoptic-XE®) containing, as a delivery system, a purified anionic heteropolysaccharide derived from gellan gum. The preparation according to the invention, referred to below as "TSP", is formulated as follows:

| timolol maleate | g | 0.684 (equal to g 0.500 of timolol) |
|---|---|---|
| TSP | g | 2.000 |
| mannitol | g | 5.000 |
| sodium merthiolate | g | 0.002 |
| deionised water | | q.s. to 100 |

TABLE 11

Ophthalmic preparations employed in the tests

| Preparation | Active ingredient | Kind (and wt. % concentration) of polymer |
|---|---|---|
| RS | Timolol 0.5% | none |
| TSP | Timolol 0.5% | TSP 2.0% |
| GELLAN | Timolol 0.5% | anionic heteropolysaccharide derived from gellan gum |

The tests have been carried out on pigmented rabbits weighing 2.0–2.5 kg. 50 μl of the preparation under study were instilled in the lower conjunctival sac of both eyes of the rabbits (at least 4 animals for each preparation and for each time tested). After 5 minutes from the administration, a blood sample was taken from the marginal vein of each rabbit's ear. After fixed time intervals (i.e., 10, 30, 60, 120, 180 and 240 min.) the animals were sacrificed with an overdose of thiopental sodium administered through the marginal vein of the ear. The eyeball was explanted and another sample of blood was taken. Cornea, iris and ciliary body were separated from the explanted eyeball (with iris and ciliary body as a whole, due to the difficulty of separating them from each other), as well as an aliquot of 150–200 μl of aqueous. The dissection of both eyes was completed in 10 minutes.

The concentrations of timolol (as base) as detected in the explanted cornea, in the irido-ciliary body, in the aqueous as well as in plasma are plotted as a function of time in FIGS. 8–11, respectively, for each one of the tested groups. Each of the data shown in the graphs represents the average of at least 4 determinations, the standard error being shown by vertical bars on each experimental point. The pharmacokinetic parameters of timolol in the various tissues examined and for the various formulations tested have been calculated from the experimental results, and are shown in the following tables. The said parameters are as follows:

$C_{max}$: maximum drug concentration $t_{max}$: time in which $C_{max}$ is reached $K_e$: apparent clearance velocity constant AUC: area under the curve of drug concentration as a function of time MRT: mean residence time of the drug in the ocular tissue or in plasma

TABLE 12

Pharmacokinetic parameters of timolol in the cornea

| Prepn. | $C_{max}$ (μg/ml ± s.e.) | $t_{max}$ (min) | $K_e$ (min$^{-1}$ 10$^2$) | AUC (min · μg/ μl ± s.e.) | MRT (min) |
|---|---|---|---|---|---|
| RS | 28.51 ± 2.69 | 10 | 1.15 | 3193.6 ± 529.5 | 68.92 |
| GELLAN | 68.35 ± 8.23 | 10 | 0.788 | 4478.9 ± 825.5 | 64.95 |
| TSP | 54.74 ± 11.71 | 30 | 1.68 | 5122.8 ± 1094.8 | 55.19 |

TABLE 13

Pharmacokinetic parameters of timolol in the irido-ciliary body

| Prepn. | $C_{max}$ (μg/ml ± s.e.) | $t_{max}$ (min) | $K_e$ (min$^{-1}$ 10$^2$) | AUC (min · μg/ μl ± s.e.) | MRT (min) |
|---|---|---|---|---|---|
| RS | 65.81 ± 6.01 | 30 | 0.610 | 5806.9 ± 848.9 | 76.60 |
| GELLAN | 55.96 ± 2.21 | 120 | 0.389 | 10554.2 ± 1044.2 | 99.21 |
| TSP | 56.64 ± 2.53 | 60 | 0.589 | 9100.2 ± 1017.3 | 86.13 |

TABLE 14

Pharmacokinetic parameters of timolol in the aqueous humor

| Prepn. | $C_{max}$ (μg/ml ± s.e.) | $t_{max}$ (min) | $K_e$ (min$^{-1}$ 10$^2$) | AUC (min · μg/ μl ± s.e.) | MRT (min) |
|---|---|---|---|---|---|
| RS | 2.11 ± 0.27 | 30 | 1.24 | 141.97 ± 18.58 | 46.52 |
| GELLAN | 3.54 ± 0.62 | 60 | 1.87 | 344.54 ± 60.53 | 50.42 |
| TSP | 3.41 ± 0.26 | 60 | 1.57 | 312.64 ± 44.35 | 51.95 |

TABLE 15

Pharmacokinetic parameters of timolol in plasma

| Prepn. | $C_{max}$ (μg/ml ± s.e.) | $t_{max}$ (min) | $K_e$ (min$^{-1}$ 10$^2$) | AUC (min · μg/ μl ± s.e.) | MRT (min) |
|---|---|---|---|---|---|
| RS | 1.89 ± 0.73 | 5 | 1.70 | 46.7 ± 40.89 | 40.76 |
| GELLAN | 0.39 ± 0.24 | 5 | 5.38 | 5.67 ± 4.93 | 12.88 |
| TSP | 0.59 ± 0.34 | 5 | 3.58 | 10.5 ± 6.37 | 19.36 |

Figure 8:
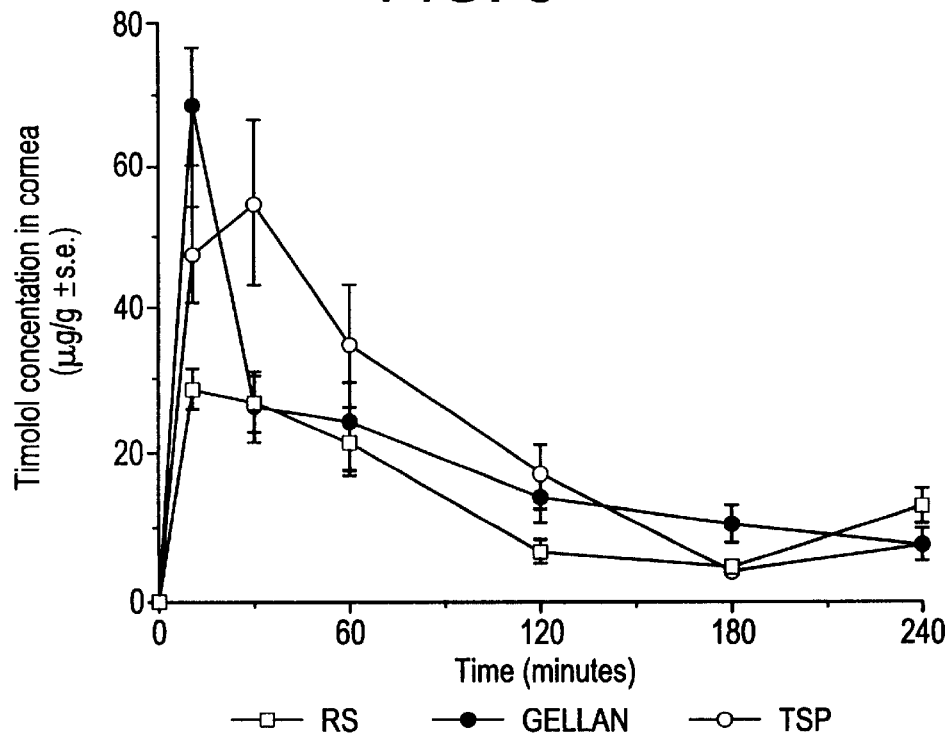
FIG. 8 shows the curves of timolol concentration versus time in the cornea of rabbits treated with timolol preparations containing or not the product according to the invention.

From the diagram of FIG. 8 it is seen that timolol concentration in the corneas reaches its peak levels after a short time from administration (i.e. 10 min., which are prolonged to 30 min. for the preparation according to the invention) and then rapidly decreases. The mean residence times are of the order of 60 min. for all of the preparations, and decrease in the following order. RS>GELLAN>TSP.

Figure 9:
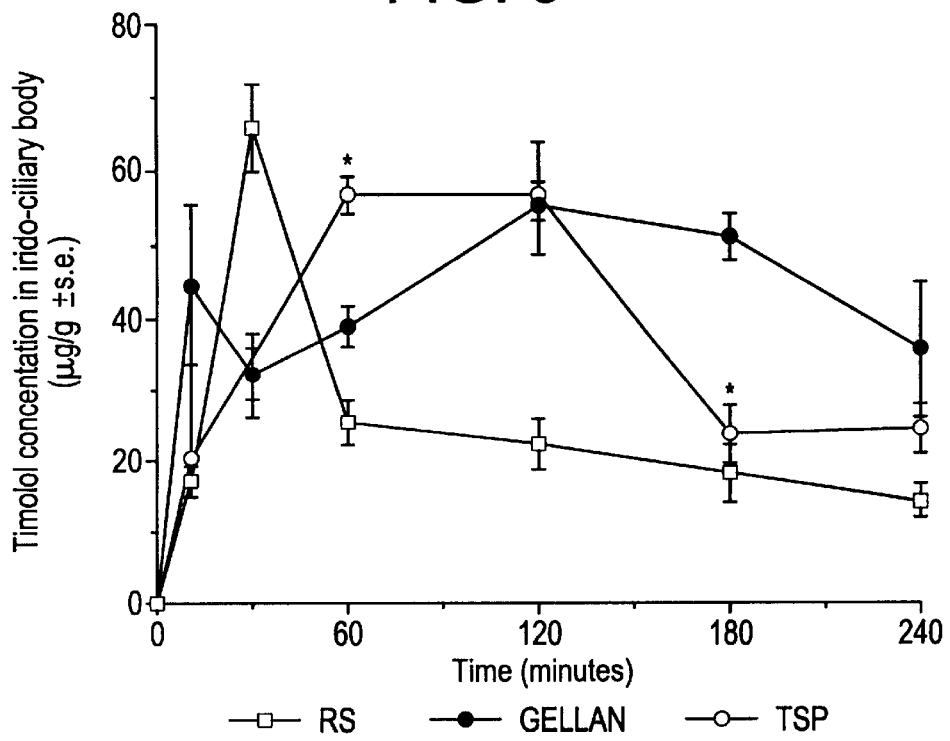
FIG. 9 shows the curves of timolol concentration versus time in the irido-ciliary body of the same rabbits of FIG. 8.

Timolol concentration is higher in the irido-ciliary body (see FIG. 9) than in the other tissues investigated (as it is evident by comparing the AUC values in tables 12–15). The difference is particularly remarkable at longer times after administration (i.e. 120 to 240 minutes). This phenomenon, which is surely due to the binding of the drug to the melanin pigments present in this area, is quite important from the therapeutical point of view, as the ciliary body is the site of action of timolol. As shown in FIG. 9, the non-viscosified aqueous solution (RS) offers the maximum concentration of timolol in the ciliary body in about 30 minutes from the administration, while the use of the two viscous vehicles (i.e., TSP and GELLAN) results in said maximum concentration being reached after 60 and 120 min., respectively. Further, the AUC values obtained for the preparations containing the said two vehicles are, respectively, 1.57 and 1.82 times greater than the AUC obtained with the aqueous solution, and the MRT values show a longer residence of timolol in the irido-ciliary body when one of the said delivery systems is used.

Figure 10:
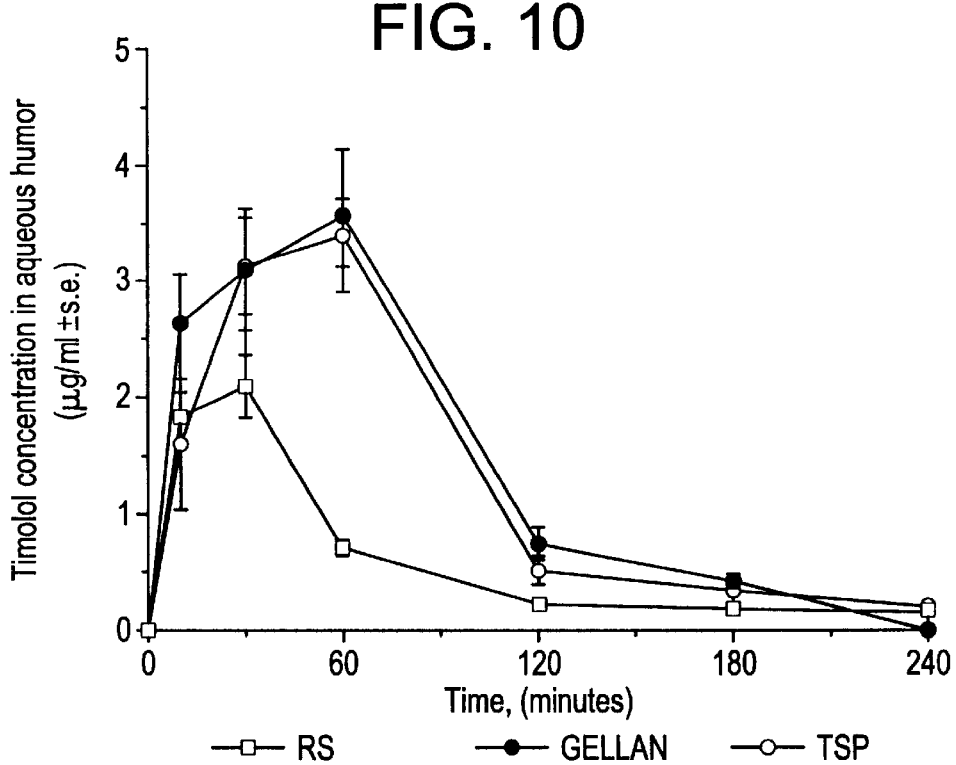
FIG. 10 shows the curves of timolol concentration versus time in the aqueous humor of the same rabbits of FIG. 8.

The concentration profiles of timolol in the aqueous humor, for the various formulations tested, are shown in FIG. 10. Also in this case, the aqueous solution offers a quantitatively moderate peak level after a short time from administration (i.e. 30 min.), while TSP and GELLAN allow to reach higher peak levels, after a prolonged time (i.e., 60 minutes). The pharmacokinetic parameters of timolol in the aqueous humor (Table 14) show an extremely similar behaviour of the two viscosified carriers.

Figure 11:
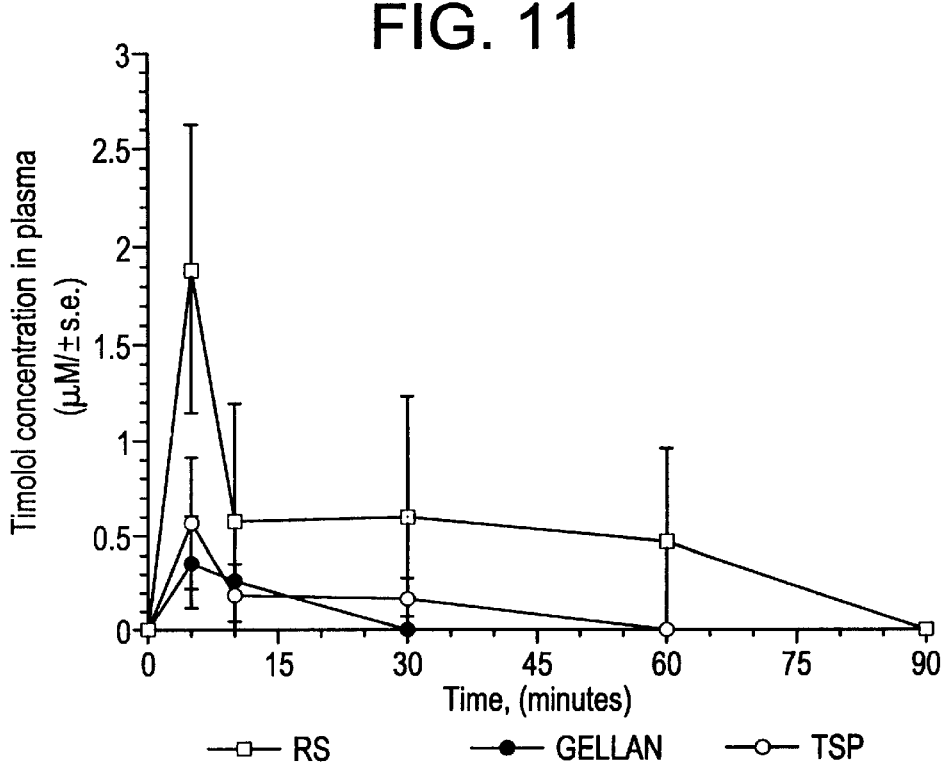
FIG. 11 shows the curves of timolol concentration versus time in the plasma of the same rabbits of FIG. 8.

As to the level reached by timolol in the blood upon the concerned topical administration, FIG. 11 shows that with the non-thickened reference solution considerable blood levels are reached, while with the two delivery systems much smaller AUC values are obtained. As shown in Table 15, the clearance of the drug from the blood is faster when viscous delivery systems are combined therewith. This is confirmed by the much shorter half-lives in blood found for the TSP and GELLAN preparations.

Antibiotic Formulations

Also in the use of antibiotics, the most critical problem to overcome in order to achieve a satisfactory therapeutic effect in treating ophthalmic conditions is how to obtain, at the desired site of action, drug concentrations above the minimum effective one. This is particularly true in the case of corneal infections, as corneal epithelium offers a remarkable resistance to the passage of polar or scarcely lipophylic molecules. More than 80% of all bacterial keratites are originated by *Staphylococcus aureus, Streptococcus pneumoniae* and *Pseudomonas aeruginosa*. Such microorganisms are endowed with notable adhesive properties, and the high occurrence of keratites is considered to be connected with the ability of said micro-organisms to adhere to the corneal epithelium. The therapeutical approach in such situations normally consists in the use of combinations of antibiotics or in the use of "fortified" galenic preparations, containing higher concentrations of active ingredient than the commercial medicaments. Such higher concentrations are not used in ordinary commercial products due to their ocular toxicity. In spite of the various attempts that have been made in order to enhance the corneal permeation of antibiotic drugs, serious forms of keratitis are still difficult to resolve. In view of the foregoing, the experimental activity reported below was directed to ascertain whether the polysaccharide according to the invention, being adhesive to the mucin layer normally present on the corneal epithelium, is effective in enhancing the corneal penetration of topical antibiotics.

Two different topical ophthalmic antibiotics, i.e. gentamicin and ofloxacin, have been tested in combination with the delivery system according to the invention. For each one of the said drugs a non-viscosified reference preparation, referred to in the following tables as RS (i.e. reference solution) was employed for comparison. The gentamicin RS is a commercial eye-drop preparation (i.e., Ribomicin®) containing 0.3% by weight of gentamicin (as gentamicin sulphate), while the ofloxacin RS is a commercial eye-drop preparation (i.e., Exocin®) containing 0.3% by weight of ofloxacin. The two preparations according to the invention (both referred to as "TSP" to distinguish them from the corresponding aqueous solutions) are formulated as follows:

| ◊ Gentamicin formulation | |
| --- | --- |
| gentamicin sulphate | g 0.500 |
|  | (equal to g 0.30 of gentamicin) |
| TSP | g 2.000 |
| mannitol | g 5.000 |
| sodium merthiolate | g 0.002 |
| deionised water | q.s. to 100 |
| NaOH | q.s. to pH = 6.7 |

The addition of NaOH was required since the initial pH was 4.5. The final osmolarity was 324 mOsm/kg.

| ◊ Ofloxacin formulation | |
| --- | --- |
| ofloxacin | g 0.300 |
| TSP | g 2.000 |
| mannitol | g 5.000 |
| sodium merthiolate | g 0.002 |
| deionised water | q.s. to 100 |
| NaOH | q.s. to pH 7.6 |

The addition of NaOH was required in order to solublise the active ingredient. The final osmolarity was 298 mOsm/kg.

The tests have been carried out on New Zealand albino rabbits weighing 2–2.5 kg. 50 μl of the preparation under study were instilled in the lower conjunctival sac of both eyes of the rabbits (at least 4–5 animals for each preparation and for each time tested). The product was instilled 12 times in total, at 30 minutes intervals. After fixed time intervals (i.e., 30, 60, 120 and 180 min.) from the last administration, the animals were sacrificed with an overdose of ethyl urethane and the aqueous humor was taken from their eyes by paracentesis, in order to evaluate the drug concentrations therein. The corneal concentrations of the drugs were evaluated only on the animals sacrificed after 60 minutes from the last administration. To this end, the explanted corneas were homogenised and treated by centrifugation.

In order to evaluate the extent of penetration of the two active ingredients through the cornea, the antibacterial activity of the corneal extracts and of the aqueous was measured by means of a microbiological assay. *Bacillus subtilis* ATCC 6638, a standard ATCC strain which is frequently used as a reference to evaluate the concentration of amino-glycoside and fluorinated quinolone antibacterials, was cultured for one week in an appropriate medium. The resulting spore suspension was diluted to a fixed concentration and aliquots of the diluted spore suspension were placed in Petri dishes containing suitable agar mediums. Small incisions were made in the agar to obtain cavities in which samples of aqueous or of cornea were placed. The plates were incubated for one day at 37° C. and the antibiotic activity of the samples was evaluated by measuring the diameter of the inhibition halo formed around the cavities. The corresponding concentrations of gentamicin and ofloxacin were determined by means of calibration curves obtained with known amounts of the said drugs. The minimum detectable gentamicin concentration was 0.03 µg/ml, while for ofloxacin the minimum detectable concentration was 0.08 µg/ml.

Figure 12:
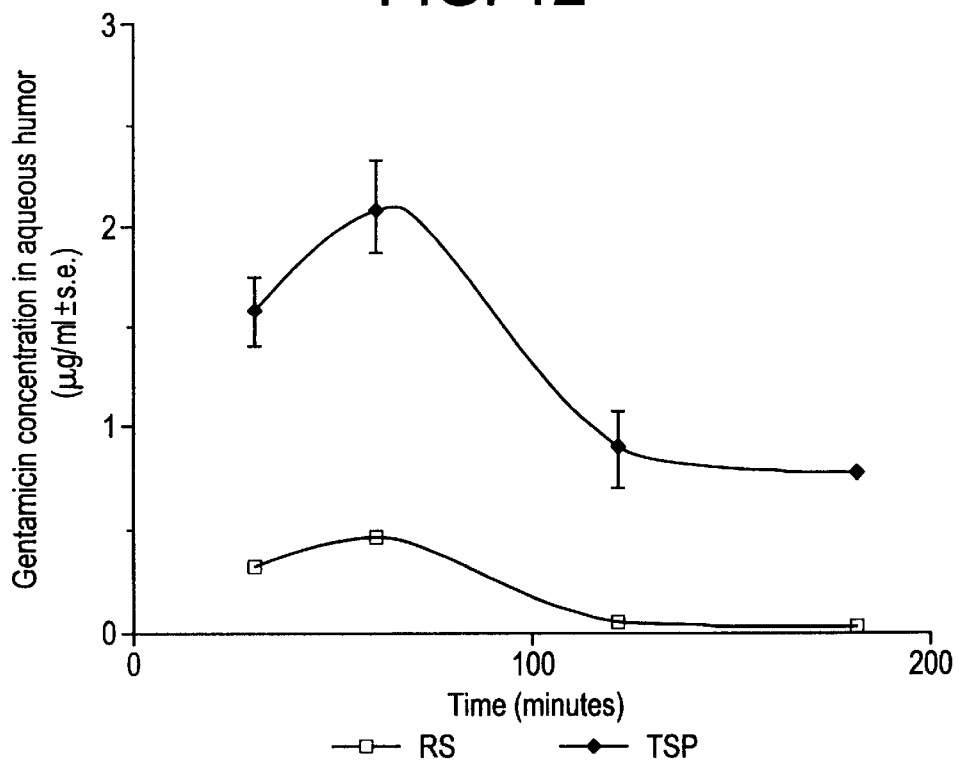
FIG. 12 shows the curves of gentamicin concentration versus time in the aqueous humor of rabbits treated with gentamicin preparations containing or not the product according to the invention.

The results obtained from the above tests are summarised in FIGS. 12 and 13, as well as in the following Tables 16–19 as concerns the drug concentrations detected in the aqueous, and in Tables 20–21 as concerns the concentrations detected in the cornea. Specifically, Table 16 below shows the numerical data corresponding to the graph of FIG. 12, comparing the gentamicin levels obtained in the aqueous upon administration of the reference solution with those obtained by using the tamarind seed polysaccharide vehicle according to the invention.

TABLE 16

Average concentrations of gentamicin detected in aqueous

| Time (min.) | RS gentamicin concentrations (µg/ml) | TSP | significance (Student's t-test) |
|---|---|---|---|
| 30 | 0.328 ± 0.130 | 1.590 ± 0.176 | 0.000 |
| 60 | 0.474 ± 0.131 | 2.108 ± 0.229 | 0.000 |
| 120 | 0.053 ± 0.009 | 0.900 ± 0.187 | 0.004 |
| 180 | 0.035 ± 0.006 | 0.787 ± 0.015 | 0.000 |

On the basis of the above data, the following pharmacokinetic parameters of gentamicin, in the two formulations tested, were calculated:

TABLE 17

Pharmacokinetic parameters of gentamicin in aqueous

| Prepn. | $C_{max}$ (µg/ml ± s.e.) | $t_{max}$ (min) | $K_e$ ($min^{-1}$ $10^2$) | AUC (min · µg/ µl ± s.e.) | MRT (min) |
|---|---|---|---|---|---|
| RS | 0.47 ± 0.13 | 60 | 2.17 | 35.37 ± 10.58 | 45.91 |
| TSP | 2.11 ± 0.23 | 60 | 0.82 | 220.18 ± 27.29 | 59.74 |

Figure 13:
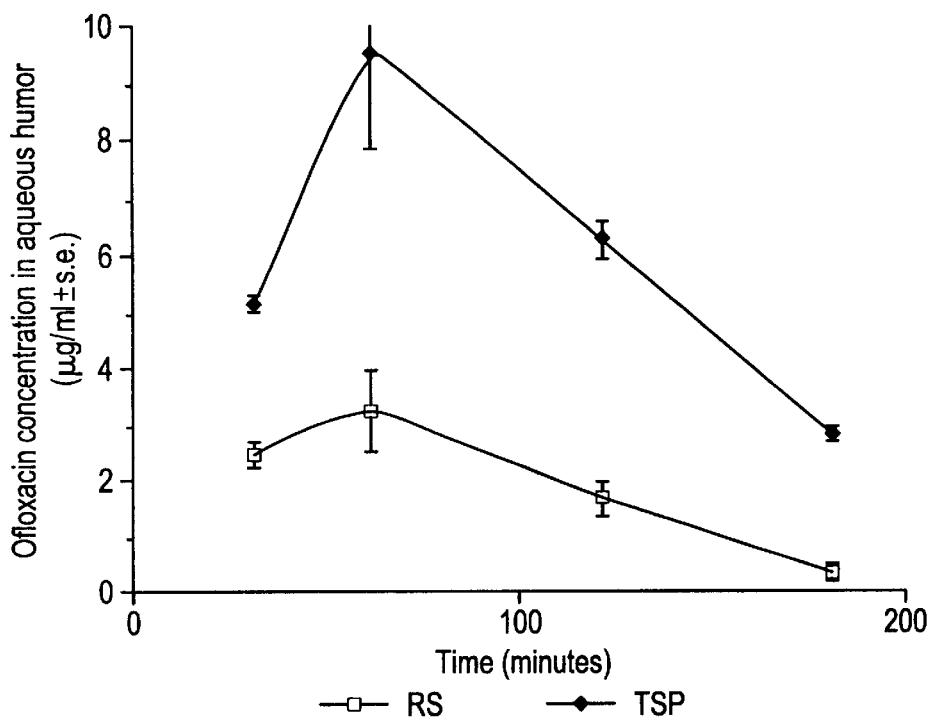
FIG. 13 shows the curves of ofloxacin concentration versus time in the aqueous humor of rabbits treated with ofloxacin preparations containing or not the product according to the invention.

Similarly, Tables 18 and 19 show, respectively, the numerical data corresponding to the graph of FIG. 13 (comparing the ofloxacin levels obtained in the aqueous upon administration of the reference solution with those obtained by using the vehicle according to the invention) and the pharmacokinetic parameters calculated therefrom.

TABLE 18

Average concentrations of ofloxacin detected in aqueous

| Time (min.) | RS ofloxacin concentrations (µg/ml) | TSP | significance (Student's t-test) |
|---|---|---|---|
| 30 | 2.475 ± 0.225 | 5.150 ± 0.144 | 0.000 |
| 60 | 3.240 ± 0.723 | 9.540 ± 1.677 | 0.009 |

TABLE 18-continued

Average concentrations of ofloxacin detected in aqueous

| Time (min.) | RS ofloxacin concentrations (µg/ml) | TSP | significance (Student's t-test) |
|---|---|---|---|
| 120 | 1.700 ± 0.308 | 6.300 ± 0.334 | 0.000 |
| 180 | 0.350 ± 0.144 | 0.285 ± 0.118 | 0.000 |

TABLE 19

Pharmacokinetic parameters of ofloxacin in aqueous

| Prepn. | $C_{max}$ (µg/ml ± s.e.) | $t_{max}$ (min) | $K_e$ ($min^{-1}$ $10^2$) | AUC (min · µg/ µl ± s.e.) | MRT (min) |
|---|---|---|---|---|---|
| RS | 3.24 ± 0.72 | 60 | 1.85 | 332.55 ± 62.10 | 56.66 |
| TSP | 9.54 ± 1.68 | 60 | 1.01 | 1046.55 ± 103.38 | 64.95 |

The drug concentrations detected in the corneal tissue explanted from rabbits sacrificed after 60 minutes from the last administration of drug are reported in the two following tables.

TABLE 20

Average concentrations of gentamicin detected in cornea

| Time (min.) | RS gentamicin concentrations (µg/ml) | TSP | significance (Student's t-test) |
|---|---|---|---|
| 60 | 12.84 ± 3.250 | 36.400 ± 6.306 | 0.011 |

TABLE 21

Average concentrations of ofloxacin detected in cornea

| Time (min.) | RS ofloxacin concentrations (µg/ml) | TSP | significance (Student's t-test) |
|---|---|---|---|
| 60 | 22.32 ± 4.755 | 70.92 ± 17.577 | 0.028 |

The experimental results summarised in the foregoing clearly show a significant increase in the concentration of drug within the corneal tissues and in the aqueous humor when the active ingredient is combined with the delivery system based on tamarind seed polysaccharide according to the invention. By the use of such vehicle the rate of permeation of antimicrobial ophthalmic drugs through the cornea, and hence their bioavailability, may be greatly enhanced.

We claim:

1. A method for treating dry eye syndrome, comprising topically administering to an eye of an animal in need thereof a viscosified ophthalmic solution comprising an effective amount of a polysaccharide fraction of tamarind gum.

2. The method according to claim 1, wherein said ophthalmic solution contains from about 0.1 to about 5.0% by weight of said polysaccharide fraction of tamarind gum.

3. The method according to claim 2, wherein said ophthalmic solution contains from about 0.7 to about 1.5% by weight of said polysaccharide fraction of tamarind gum.

4. The method according to claim 3, wherein said ophthalmic solution contains about 1% by weight of said polysaccharide fraction of tamarind gum.

5. The method according to claim 1, wherein said polysaccharide fraction of tamarind gum is obtained by purification from commercial tamarind gum.

6. A method of delivering a topical ophthalmic drug to the eye, comprising topically administering to an eye of an animal in need thereof a composition comprising an effective amount of said drug and a polysaccharide fraction of tamarind gum.

7. The method according to claim 6, wherein said composition contains from about 0.1 to about 5% by weight of said polysaccharide fraction of tamarind gum.

8. The method according to claim 7, wherein said composition contains from about 1 to about 4% by weight of said polysaccharide fraction of tamarind gum.

9. The method according to claim 6, wherein said composition is in liquid form, and contains from about 1.5 to about 2.5% by weight of said polysaccharide fraction of tamarind gum.

10. The method according to claim 6, wherein said composition is in gel form, and contains from about 3 to about 4% by weight of said polysaccharide fraction of tamarind gum.

11. The method according to claim 6, wherein said polysaccharide fraction of tamarind gum is obtained by purification from commercial tamarind gum.

12. The method according to claim 6, wherein said drug is chosen from the group consisting of pilocarpine, timolol, ofloxacin and gentamicin.

13. A method of delivering one or more topical ophthalmic drugs to the eye, comprising topically administering to an eye of an animal in need thereof a composition comprising an effective amount of one or more of said drugs and a polysaccharide fraction of tamarind gum.

14. The method according to claim 13, wherein said composition contains from about 1 to about 4% by weight of said polysaccharide fraction of tamarind gum.

15. The method according to claim 13, wherein one or more of said drugs is chosen from the group consisting of pilocarpine, timolol, ofloxacin and gentamicin.

16. The method according to claim 13, wherein said polysaccharide fraction of tamarind gum is obtained by purification from commercial tamarind gum.

17. An ophthalmic formulation, comprising:
an effective amount of a purified polysacharide fraction of tamarind gum, and
an ophthalmologically acceptable solution.

18. The ophthalmic formulation according to claim 17, wherein said purified polysaccharide fraction of tamarind gum comprises from about 0.1% to about 5.0% by weight of said ophthalmic formulation.

19. The ophthalmic formulation according to claim 17, wherein said polysaccharide fraction of tamarind gum comprises from about 0.7% to about 1.5% by weight of said ophthalmic formulation.

20. The ophthalmic formulation according to claim 17, wherein said purified polysaccharide fraction of tamarind gum comprises from about 1% to about 4% by weight of said ophthalmic formulation.

21. A sustained release topical ophthalmic formulation, comprising:
an effective amount of one or more pharmaceutically active ingredients, and
an effective amount of a purified polysaccharide fraction of tamarind gum.

22. The ophthalmic formulation according to claim 21, wherein said purified polysaccharide fraction of tamarind gum comprises from about 1% to about 4% by weight of said ophthalmic formulation.

23. The ophthalmic formulation according to claim 21, wherein said one or more pharmaceutically active ingredients are chosen from the group consisting of pilocarpine, timolol, ofloxacin and gentamicin.

24. An artificial tear formulation, comprising:
an effective amount of a purified polysaccharide fraction of tamarind gum, and
an ophthalmologically acceptable solution.

25. The artificial tear formulation according to claim 24, wherein said purified polysaccharide fraction of tamarind gum comprises from about 0.1% to about 5.0% by weight of said formulation.

26. The artificial tear formulation according to claim 24, wherein said purified polysaccharide fraction of tamarind gum comprises from about 0.7% to about 1.5% by weight of said formulation.

27. The artificial tear formulation according to claim 24, wherein said purified polysaccharide fraction of tamarind gum comprises from about 1% to about 4% by weight of said formulation.

* * * * *